US009138572B2

(12) United States Patent
Zeytoonian et al.

(10) Patent No.: US 9,138,572 B2
(45) Date of Patent: Sep. 22, 2015

(54) MEDICAL VALVE WITH FLUID VOLUME ALTERATION

(75) Inventors: Paul Zeytoonian, Sudbury, MA (US); Ian Kimball, Clinton, MA (US)

(73) Assignee: NP Medical Inc., Clinton, MA (US)

( * ) Notice: Subject to any disclaimer, the term of this patent is extended or adjusted under 35 U.S.C. 154(b) by 765 days.

(21) Appl. No.: 12/822,753

(22) Filed: Jun. 24, 2010

(65) Prior Publication Data

US 2011/0319859 A1  Dec. 29, 2011

(51) Int. Cl.
| A61M 5/14 | (2006.01) |
| A61M 39/04 | (2006.01) |
| A61M 39/26 | (2006.01) |

(52) U.S. Cl.
CPC .............. *A61M 39/045* (2013.01); *A61M 39/26* (2013.01); *A61M 2039/262* (2013.01)

(58) Field of Classification Search
CPC ......... E03C 1/0401; F16K 25/02; F16K 1/00; A61M 39/04; A61M 39/20; A61M 39/26; A61M 39/39; A61M 39/045; A61M 1/0039; A61M 25/1018; F16L 37/23; F16L 37/252; F16L 37/40; A01J 5/044; A61B 17/3462; A61J 1/10
USPC .............. 137/15.01, 15.07; 251/149.1–149.8; 604/167.02, 167.03, 244, 246, 247, 604/249, 256, 403, 48, 533, 99.02
See application file for complete search history.

(56) References Cited

U.S. PATENT DOCUMENTS

| 2,594,405 A | 4/1952 | Deters .............................. 137/53 |
| 2,693,801 A | 11/1954 | Foreman ....................... 128/214 |
| 2,705,501 A | 4/1955 | Fritzsch et al. ............... 137/112 |
| 2,756,740 A | 7/1956 | Deane ................................ 128/1 |
| 2,899,975 A | 8/1959 | Fernandez ................ 137/543.17 |
| 2,919,935 A | 1/1960 | Nyberg ............................ 284/18 |
| 2,999,499 A | 9/1961 | Willet ............................ 128/214 |
| 3,087,492 A | 4/1963 | Garth et al. .................... 128/350 |
| 3,105,511 A | 10/1963 | Murphy, Jr. .................... 137/399 |
| 3,192,949 A | 7/1965 | De See ........................... 137/540 |
| 3,279,497 A | 10/1966 | Norton et al. ............. 137/614.03 |
| 3,385,301 A | 5/1968 | Harautuneian ................ 128/349 |
| 3,399,677 A | 9/1968 | Gould et al. ................... 128/349 |

(Continued)

FOREIGN PATENT DOCUMENTS

| EP | 0 268 480 A1 | 5/1988 | ............ A61M 25/00 |
| EP | 0 629 418 A2 | 12/1994 | ............ A61M 39/04 |

(Continued)

OTHER PUBLICATIONS

US 6,971,630, Dec. 2005, Leinsing et al. (withdrawn).

(Continued)

*Primary Examiner* — Scott Medway
(74) *Attorney, Agent, or Firm* — Sunstein Kann Murphy & Timbers LLP

(57) ABSTRACT

A medical valve has an open mode that permits fluid flow, and a closed mode that prevents fluid flow. To that end, the medical valve has a housing having an inlet and an outlet, and a resilient member within the housing. The resilient member has a body portion with a free state when undeformed by external mechanical forces and a deformed state when the valve is in the closed mode. The body portion is formed to return toward the free state as the valve transitions from the closed mode to the open mode and defining at least part of a fluid path through the valve.

41 Claims, 10 Drawing Sheets

(56) References Cited

U.S. PATENT DOCUMENTS

| | | | |
|---|---|---|---|
| 3,416,567 A | 12/1968 | von Dardel et al. | 137/604 |
| 3,423,063 A | 1/1969 | German | 251/149.6 |
| 3,506,005 A | 4/1970 | Gilio et al. | 128/214 |
| 3,538,950 A | 11/1970 | Porteners | 137/608 |
| 3,570,484 A | 3/1971 | Steer et al. | 128/214 |
| 3,572,375 A | 3/1971 | Rosenberg | 137/512 |
| 3,618,892 A | 11/1971 | Sciuto, Jr. | 251/149.2 |
| 3,726,282 A | 4/1973 | Patel | 128/349 BV |
| 3,806,086 A | 4/1974 | Cloyd | 251/149.7 |
| 3,831,629 A | 8/1974 | Mackal et al. | 137/525 |
| 3,838,843 A | 10/1974 | Bernhard | 251/149.1 |
| 3,921,656 A | 11/1975 | Meisenheimer, Jr. et al. | 137/68 |
| 3,923,065 A | 12/1975 | Nozick et al. | 128/348 |
| 3,965,910 A | 6/1976 | Fischer | 128/349 R |
| 3,994,293 A | 11/1976 | Ferro | 128/214 R |
| 4,063,555 A | 12/1977 | Ulinder | 128/214 R |
| 4,080,965 A | 3/1978 | Phillips | 128/214 D |
| 4,094,195 A | 6/1978 | Friswell et al. | 73/422 GC |
| 4,094,196 A | 6/1978 | Friswell | 73/422 GC |
| 4,116,201 A | 9/1978 | Shah | 128/351 |
| 4,121,585 A | 10/1978 | Becker, Jr. | 128/214 R |
| 4,143,853 A | 3/1979 | Abramson | 251/149.1 |
| 4,181,149 A | 1/1980 | Cox | 137/614.02 |
| 4,223,808 A | 9/1980 | Williams et al. | 222/88 |
| 4,300,571 A | 11/1981 | Waldbillig | 128/673 |
| 4,324,239 A | 4/1982 | Gordon et al. | 128/214 R |
| 4,333,455 A | 6/1982 | Bodicky | 128/214.4 |
| 4,334,551 A | 6/1982 | Pfister | 137/614.03 |
| 4,335,747 A | 6/1982 | Mitsumoto et al. | 137/614.06 |
| 4,344,435 A | 8/1982 | Aubin | 128/350 R |
| 4,387,879 A | 6/1983 | Tauschinski | 251/149.1 |
| 4,401,432 A | 8/1983 | Schwartz | 604/89 |
| 4,421,296 A | 12/1983 | Stephens | 251/149.7 |
| 4,445,664 A | 5/1984 | Allread | 251/149.2 |
| 4,458,480 A | 7/1984 | Irwin | 60/39.63 |
| 4,473,211 A | 9/1984 | Fremy | 251/149.2 |
| 4,496,348 A | 1/1985 | Genese et al. | 604/167 |
| 4,498,658 A | 2/1985 | Mikiya | 251/149.6 |
| 4,534,758 A | 8/1985 | Akers et al. | 604/85 |
| 4,535,820 A | 8/1985 | Raines | 137/854 |
| 4,550,785 A | 11/1985 | Hibbard et al. | 173/134 |
| 4,551,136 A | 11/1985 | Mandl | 604/141 |
| 4,585,435 A | 4/1986 | Vaillancourt | 604/27 |
| 4,596,557 A | 6/1986 | Pexa | 604/86 |
| 4,611,973 A | 9/1986 | Birdwell | 417/342 |
| 4,617,015 A | 10/1986 | Foltz | 604/100 |
| 4,627,598 A | 12/1986 | Fremy | 251/149.2 |
| 4,661,110 A | 4/1987 | Fortier et al. | 604/256 |
| 4,664,149 A | 5/1987 | Fremy | 137/614.06 |
| 4,675,003 A | 6/1987 | Hooven | 604/9 |
| 4,681,132 A | 7/1987 | Lardner | 137/271 |
| 4,683,905 A | 8/1987 | Vigneau et al. | 137/329.1 |
| 4,683,916 A | 8/1987 | Raines | 137/854 |
| 4,698,061 A | 10/1987 | Makaryk et al. | 604/408 |
| 4,710,168 A * | 12/1987 | Schwab et al. | 604/99.02 |
| 4,712,583 A | 12/1987 | Pelmulder et al. | 137/852 |
| 4,743,235 A | 5/1988 | Waldbillig et al. | 604/250 |
| 4,745,950 A | 5/1988 | Mathieu | 137/798 |
| 4,749,003 A | 6/1988 | Leason | 137/854 |
| 4,752,287 A | 6/1988 | Kurtz et al. | 604/99 |
| 4,752,292 A | 6/1988 | Lopez et al. | 604/244 |
| 4,758,224 A | 7/1988 | Siposs | 604/119 |
| 4,776,369 A | 10/1988 | Lardner et al. | 137/515.5 |
| 4,809,679 A | 3/1989 | Shimonaka et al. | 128/4 |
| 4,816,020 A | 3/1989 | Brownell | 604/97 |
| 4,819,684 A | 4/1989 | Zaugg et al. | 137/112 |
| 4,830,331 A | 5/1989 | Vindum | 251/63 |
| 4,842,591 A | 6/1989 | Luther | 604/256 |
| 4,850,978 A | 7/1989 | Dudar et al. | 604/201 |
| 4,874,377 A | 10/1989 | Newgard et al. | 604/167 |
| 4,905,965 A | 3/1990 | Dolev | 251/149.9 |
| 4,909,798 A * | 3/1990 | Fleischhacker et al. | 604/256 |
| 4,915,687 A | 4/1990 | Sivert | 604/83 |
| 4,917,668 A * | 4/1990 | Haindl | 604/167.03 |
| 4,935,010 A | 6/1990 | Cox et al. | 604/122 |
| 4,944,329 A | 7/1990 | Cardin et al. | 137/614.05 |
| 4,966,199 A | 10/1990 | Ruschke | 137/843 |
| 5,006,114 A | 4/1991 | Rogers et al. | 604/167 |
| 5,041,087 A | 8/1991 | Loo et al. | 604/83 |
| 5,048,537 A | 9/1991 | Messinger | 128/673 |
| 5,049,128 A | 9/1991 | Duquette | 604/83 |
| 5,050,841 A | 9/1991 | Jacobsson | 251/149.9 |
| 5,059,175 A | 10/1991 | Hanover et al. | 604/891.1 |
| 5,064,416 A * | 11/1991 | Newgard et al. | 604/167.03 |
| 5,065,783 A | 11/1991 | Ogle, II | 137/68.1 |
| 5,080,654 A | 1/1992 | Picha et al. | 604/167 |
| 5,085,645 A * | 2/1992 | Purdy et al. | 604/167.03 |
| 5,098,394 A | 3/1992 | Luther | 604/167 |
| 5,100,394 A | 3/1992 | Dudar et al. | 604/283 |
| 5,108,380 A * | 4/1992 | Herlitze et al. | 604/533 |
| 5,122,123 A | 6/1992 | Vaillancourt | 604/192 |
| 5,135,489 A * | 8/1992 | Jepson et al. | 604/48 |
| 5,147,333 A | 9/1992 | Raines | 604/249 |
| 5,163,922 A * | 11/1992 | McElveen et al. | 604/249 |
| 5,171,230 A | 12/1992 | Eland et al. | 604/250 |
| 5,184,652 A | 2/1993 | Fan | 141/21 |
| 5,190,067 A | 3/1993 | Paradis et al. | 137/1 |
| 5,199,947 A | 4/1993 | Lopez et al. | 604/56 |
| 5,201,715 A | 4/1993 | Masters | 604/175 |
| 5,203,775 A | 4/1993 | Frank et al. | 604/256 |
| 5,215,538 A | 6/1993 | Larkin | 604/249 |
| 5,221,271 A | 6/1993 | Nicholson et al. | 604/283 |
| 5,230,706 A | 7/1993 | Duquette | 604/83 |
| 5,242,393 A | 9/1993 | Brimhall et al. | 604/86 |
| 5,242,432 A | 9/1993 | DeFrank | 604/284 |
| 5,269,771 A | 12/1993 | Thomas et al. | 604/213 |
| 5,280,876 A | 1/1994 | Atkins | 251/149.1 |
| 5,289,849 A | 3/1994 | Paradis | 137/606 |
| 5,295,657 A | 3/1994 | Atkinson | 251/149.1 |
| 5,300,034 A | 4/1994 | Behnke et al. | 604/167 |
| 5,320,328 A | 6/1994 | Decloux et al. | 251/326 |
| 5,330,435 A | 7/1994 | Vaillancourt | 604/167 |
| 5,342,315 A | 8/1994 | Rowe et al. | 604/167 |
| 5,342,326 A | 8/1994 | Peppel et al. | 604/284 |
| 5,349,984 A | 9/1994 | Weinheimer et al. | 137/543.21 |
| 5,360,413 A * | 11/1994 | Leason et al. | 604/249 |
| 5,380,306 A * | 1/1995 | Brinon | 604/244 |
| 5,390,898 A | 2/1995 | Smedley et al. | 251/149.6 |
| 5,397,310 A * | 3/1995 | Chu et al. | 604/158 |
| 5,397,314 A | 3/1995 | Farley et al. | 604/256 |
| 5,401,255 A | 3/1995 | Sutherland et al. | 604/247 |
| 5,403,284 A | 4/1995 | Gross | 604/167 |
| 5,439,451 A * | 8/1995 | Collinson et al. | 604/247 |
| 5,441,487 A | 8/1995 | Vedder | 604/167 |
| 5,456,675 A | 10/1995 | Wolbring et al. | 604/280 |
| 5,458,640 A | 10/1995 | Gerrone | 604/264 |
| 5,465,938 A | 11/1995 | Werge et al. | 251/149.1 |
| 5,470,319 A * | 11/1995 | Mayer | 604/167.02 |
| 5,474,536 A | 12/1995 | Bonaldo | 604/86 |
| 5,474,544 A | 12/1995 | Lynn | 604/283 |
| 5,487,728 A | 1/1996 | Vaillancourt | 604/86 |
| 5,489,274 A | 2/1996 | Chu et al. | 604/167 |
| 5,509,433 A | 4/1996 | Paradis | 137/1 |
| 5,509,912 A | 4/1996 | Vaillancourt et al. | 604/283 |
| 5,514,116 A | 5/1996 | Vaillancourt et al. | 604/283 |
| 5,520,666 A | 5/1996 | Choudhury et al. | 604/283 |
| 5,533,708 A | 7/1996 | Atkinson et al. | 251/149.1 |
| 5,533,983 A | 7/1996 | Haining | 604/249 |
| 5,535,771 A * | 7/1996 | Purdy et al. | 137/15.01 |
| 5,535,785 A | 7/1996 | Werge et al. | 137/843 |
| 5,540,661 A | 7/1996 | Tomisaka et al. | 604/265 |
| 5,549,566 A * | 8/1996 | Elias et al. | 604/167.03 |
| 5,549,577 A | 8/1996 | Siegel et al. | 604/256 |
| 5,555,908 A | 9/1996 | Edwards et al. | 137/329.1 |
| 5,569,209 A | 10/1996 | Roitman | 604/190 |
| 5,569,235 A * | 10/1996 | Ross et al. | 604/403 |
| 5,573,516 A | 11/1996 | Tyner | 604/249 |
| 5,578,059 A | 11/1996 | Patzer | 604/249 |
| 5,597,536 A * | 1/1997 | Mayer | 422/565 |
| 5,613,663 A | 3/1997 | Schmidt et al. | 251/149.2 |
| 5,616,129 A | 4/1997 | Mayer | 604/167 |
| 5,616,130 A * | 4/1997 | Mayer | 604/167.02 |
| 5,620,434 A | 4/1997 | Brony | 604/406 |
| 5,628,732 A | 5/1997 | Antoon, Jr. et al. | 604/167 |

(56) References Cited

U.S. PATENT DOCUMENTS

| | | | |
|---|---|---|---|
| 5,674,206 A | 10/1997 | Allton et al. | 604/249 |
| 5,676,346 A * | 10/1997 | Leinsing | 251/149.1 |
| 5,685,866 A | 11/1997 | Lopez | 604/249 |
| 5,694,686 A | 12/1997 | Lopez | 29/890.126 |
| 5,695,466 A | 12/1997 | Lopez et al. | 604/93 |
| 5,699,821 A * | 12/1997 | Paradis | 137/1 |
| 5,700,248 A | 12/1997 | Lopez | 604/249 |
| 5,730,418 A | 3/1998 | Feith et al. | 251/149.6 |
| 5,743,883 A * | 4/1998 | Visconti | 604/167.02 |
| 5,749,861 A | 5/1998 | Guala et al. | 604/249 |
| RE35,841 E | 7/1998 | Frank et al. | 604/256 |
| 5,775,671 A | 7/1998 | Cote, Sr. | 251/149.8 |
| 5,776,113 A | 7/1998 | Daugherty et al. | 604/280 |
| 5,782,816 A | 7/1998 | Werschmidt et al. | 604/256 |
| 5,788,215 A | 8/1998 | Ryan | 251/149.6 |
| 5,806,551 A | 9/1998 | Meloul et al. | 137/15 |
| 5,806,831 A | 9/1998 | Paradis | 251/149.1 |
| 5,807,348 A * | 9/1998 | Zinger et al. | 604/246 |
| 5,817,069 A | 10/1998 | Arnett | 604/256 |
| 5,820,601 A | 10/1998 | Mayer | 604/167 |
| 5,836,923 A | 11/1998 | Mayer | 604/246 |
| 5,921,264 A * | 7/1999 | Paradis | 137/15.17 |
| 5,947,954 A | 9/1999 | Bonaldo | 604/533 |
| 5,957,898 A | 9/1999 | Jepson et al. | 604/256 |
| 5,967,490 A | 10/1999 | Pike | 251/149.1 |
| 6,029,946 A | 2/2000 | Doyle | 251/149.1 |
| 6,036,171 A | 3/2000 | Weinheimer et al. | 251/149.6 |
| 6,039,302 A * | 3/2000 | Cote et al. | 251/149.1 |
| 6,048,335 A | 4/2000 | Mayer | 604/167 |
| 6,050,978 A * | 4/2000 | Orr et al. | 604/249 |
| 6,063,062 A | 5/2000 | Paradis | 604/249 |
| 6,068,011 A * | 5/2000 | Paradis | 137/1 |
| 6,079,432 A * | 6/2000 | Paradis | 137/1 |
| 6,089,539 A | 7/2000 | Kouda | 251/149.2 |
| 6,089,541 A | 7/2000 | Weinheimer et al. | 251/149.6 |
| 6,090,074 A | 7/2000 | Brimhall et al. | 604/167.05 |
| 6,113,068 A * | 9/2000 | Ryan | 251/149.4 |
| 6,117,114 A | 9/2000 | Paradis | 604/246 |
| 6,142,446 A | 11/2000 | Leinsing | 251/149.1 |
| 6,152,900 A | 11/2000 | Mayer | 604/167 |
| 6,158,458 A | 12/2000 | Ryan | 137/515.5 |
| 6,171,287 B1 * | 1/2001 | Lynn et al. | 604/256 |
| 6,183,448 B1 * | 2/2001 | Mayer | 604/256 |
| 6,189,859 B1 | 2/2001 | Rohrbough et al. | 251/149.1 |
| 6,206,860 B1 | 3/2001 | Richmond | 604/246 |
| 6,206,861 B1 | 3/2001 | Mayer | 604/246 |
| 6,221,065 B1 | 4/2001 | Davis | 604/539 |
| 6,228,069 B1 | 5/2001 | Barth et al. | 604/249 |
| 6,245,048 B1 | 6/2001 | Fangrow, Jr. et al. | 604/249 |
| 6,290,206 B1 | 9/2001 | Doyle | 251/149.1 |
| 6,299,131 B1 * | 10/2001 | Ryan | 251/149.1 |
| 6,344,033 B1 | 2/2002 | Jepson et al. | 604/256 |
| 6,364,869 B1 | 4/2002 | Bonaldo | 604/537 |
| 6,422,267 B1 | 7/2002 | Makishima et al. | 137/616.7 |
| 6,428,520 B1 | 8/2002 | Lopez et al. | 604/249 |
| 6,485,472 B1 | 11/2002 | Richmond | 604/246 |
| 6,491,668 B1 | 12/2002 | Paradis | 604/246 |
| 6,541,802 B2 | 4/2003 | Doyle | 257/149.1 |
| 6,543,745 B1 | 4/2003 | Enerson | 251/149.7 |
| 6,585,229 B2 | 7/2003 | Cote, Sr. et al. | 251/149.1 |
| 6,595,964 B2 * | 7/2003 | Finley et al. | 604/246 |
| 6,595,981 B2 | 7/2003 | Huet | 604/523 |
| 6,598,620 B1 | 7/2003 | Fremy | 137/614.03 |
| 6,609,696 B2 | 8/2003 | Enerson | 251/86 |
| 6,669,673 B2 | 12/2003 | Lopez | 604/249 |
| 6,695,817 B1 | 2/2004 | Fangrow, Jr. | 604/167.01 |
| 6,706,022 B1 * | 3/2004 | Leinsing et al. | 604/247 |
| 6,745,998 B2 | 6/2004 | Doyle | 251/149.6 |
| 6,755,391 B2 | 6/2004 | Newton et al. | 251/149.6 |
| 6,779,777 B2 | 8/2004 | Kouda | 251/149.6 |
| 6,802,490 B2 * | 10/2004 | Leinsing et al. | 251/149.6 |
| 6,811,139 B2 | 11/2004 | Hishikawa | 251/149.1 |
| 6,827,329 B2 | 12/2004 | Mikiya et al. | 251/97 |
| 6,840,501 B2 | 1/2005 | Doyle | 251/149.1 |
| 6,869,426 B2 | 3/2005 | Ganem | 604/533 |
| 6,871,838 B2 | 3/2005 | Raines et al. | 251/149.4 |
| 6,883,778 B1 | 4/2005 | Newton et al. | 251/149.1 |
| 6,892,998 B2 | 5/2005 | Newton | 251/149.1 |
| 6,899,132 B2 | 5/2005 | Mikiya et al. | 137/616.7 |
| 6,916,309 B2 | 7/2005 | Fangrow, Jr. | 604/167.01 |
| 6,932,795 B2 * | 8/2005 | Lopez et al. | 604/249 |
| 6,964,406 B2 | 11/2005 | Doyle | 251/149.6 |
| 6,991,215 B2 | 1/2006 | Kiehne | 251/149.6 |
| 7,004,934 B2 | 2/2006 | Vaillancourt | 604/533 |
| 7,008,404 B2 * | 3/2006 | Nakajima | 604/158 |
| 7,014,169 B2 | 3/2006 | Newton et al. | 251/149.6 |
| 7,028,982 B2 | 4/2006 | Kohda | 251/149.2 |
| 7,037,302 B2 | 5/2006 | Vaillancourt | 604/533 |
| 7,056,308 B2 | 6/2006 | Utterberg | 604/256 |
| 7,063,685 B2 | 6/2006 | Rome | 604/256 |
| 7,070,164 B2 | 7/2006 | Kohda | 251/149.2 |
| 7,100,890 B2 | 9/2006 | Cote, Sr. et al. | 251/149.1 |
| 7,104,520 B2 | 9/2006 | Leinsing et al. | 251/149.6 |
| 7,114,701 B2 | 10/2006 | Peppel | 251/149 |
| 7,118,560 B2 | 10/2006 | Bonaldo | 604/537 |
| 7,125,396 B2 | 10/2006 | Leinsing et al. | 604/167.03 |
| 7,131,458 B2 | 11/2006 | Kohda | 137/614.03 |
| 7,184,825 B2 | 2/2007 | Leinsing et al. | 604/20 |
| 7,244,249 B2 | 7/2007 | Leinsing et al. | 604/500 |
| 7,306,199 B2 | 12/2007 | Leinsing et al. | 251/149.6 |
| 7,314,061 B2 | 1/2008 | Peppel | 137/605 |
| 7,329,249 B2 | 2/2008 | Bonaldo | 604/537 |
| 7,343,931 B2 | 3/2008 | Packham | 137/614.04 |
| 7,357,792 B2 * | 4/2008 | Newton et al. | 604/244 |
| 7,396,348 B2 * | 7/2008 | Newton et al. | 604/256 |
| 7,497,848 B2 | 3/2009 | Leinsing et al. | 604/247 |
| 7,497,849 B2 | 3/2009 | Fangrow, Jr. | 604/247 |
| 7,510,545 B2 | 3/2009 | Peppel | 604/256 |
| 7,520,489 B2 * | 4/2009 | Ruschke et al. | 251/149.7 |
| 7,713,250 B2 * | 5/2010 | Harding et al. | 604/256 |
| 7,753,338 B2 * | 7/2010 | Desecki | 251/149.8 |
| 7,789,864 B2 * | 9/2010 | Cote et al. | 604/256 |
| 7,815,168 B2 | 10/2010 | Vangsness et al. | 251/149.2 |
| 7,824,393 B2 * | 11/2010 | Fangrow | 604/533 |
| 7,887,519 B2 * | 2/2011 | Cote et al. | 604/247 |
| 8,100,869 B2 | 1/2012 | Vangsness et al. | 604/249 |
| 8,100,885 B2 * | 1/2012 | Chebator et al. | 604/533 |
| 8,123,727 B2 * | 2/2012 | Luther et al. | 604/249 |
| 8,221,363 B2 * | 7/2012 | Jepson | 604/246 |
| 2001/0049508 A1 | 12/2001 | Fangrow, Jr. et al. | 604/256 |
| 2002/0029020 A1 | 3/2002 | Cote, Sr. et al. | 604/247 |
| 2003/0050610 A1 * | 3/2003 | Newton et al. | 604/256 |
| 2003/0093061 A1 | 5/2003 | Ganem | 604/533 |
| 2003/0098430 A1 | 5/2003 | Leinsing et al. | 251/149.6 |
| 2003/0141477 A1 | 7/2003 | Miller | 251/149.1 |
| 2004/0006330 A1 | 1/2004 | Fangrow, Jr. | 604/533 |
| 2004/0049158 A1 | 3/2004 | Ley et al. | 604/167.03 |
| 2004/0073171 A1 | 4/2004 | Rogers et al. | 604/164.13 |
| 2004/0124388 A1 | 7/2004 | Kiehne | 251/149.1 |
| 2004/0138626 A1 | 7/2004 | Cote, Sr. et al. | 604/249 |
| 2004/0173769 A1 | 9/2004 | deCler | 251/149.1 |
| 2005/0038397 A1 | 2/2005 | Newton et al. | 604/249 |
| 2005/0087239 A1 | 4/2005 | Kohda | 137/614.03 |
| 2005/0087241 A1 | 4/2005 | Kohda | 137/614.03 |
| 2005/0090805 A1 | 4/2005 | Shaw et al. | 604/523 |
| 2005/0121638 A1 | 6/2005 | Doyle | 251/149 |
| 2005/0165365 A1 | 7/2005 | Newton et al. | 604/246 |
| 2005/0222541 A1 * | 10/2005 | Lopez et al. | 604/249 |
| 2005/0228362 A1 | 10/2005 | Vaillancourt | 604/533 |
| 2005/0256457 A1 | 11/2005 | Rome | 604/167.06 |
| 2006/0108555 A1 | 5/2006 | Kiehne | 251/149.7 |
| 2006/0129109 A1 | 6/2006 | Shaw et al. | 604/246 |
| 2006/0142735 A1 | 6/2006 | Whitley | 604/357 |
| 2006/0161115 A1 | 7/2006 | Fangrow | 604/249 |
| 2006/0178645 A1 | 8/2006 | Peppel | 604/249 |
| 2006/0200072 A1 | 9/2006 | Peppel | 604/93.01 |
| 2006/0200088 A1 | 9/2006 | Lopez et al. | 604/246 |
| 2006/0200089 A1 | 9/2006 | Lopez et al. | 604/246 |
| 2006/0200090 A1 | 9/2006 | Lopez et al. | 604/246 |
| 2006/0206061 A1 | 9/2006 | Lopez et al. | 604/246 |
| 2006/0211997 A1 | 9/2006 | Fangrow | 604/246 |
| 2006/0211998 A1 | 9/2006 | Fangrow | 604/246 |
| 2006/0211999 A1 | 9/2006 | Fangrow | 604/246 |
| 2006/0217671 A1 | 9/2006 | Peppel | 604/246 |

(56) References Cited

U.S. PATENT DOCUMENTS

| | | |
|---|---|---|
| 2006/0264848 A1 | 11/2006 | Fangrow ................... 604/249 |
| 2006/0264849 A1 | 11/2006 | Lopez et al. ............... 604/249 |
| 2006/0270999 A1 | 11/2006 | Fangrow ................... 604/249 |
| 2006/0271016 A1 | 11/2006 | Fangrow ................... 604/539 |
| 2006/0293629 A1 | 12/2006 | Cote, Sr. et al. ........... 604/246 |
| 2007/0012893 A1 | 1/2007 | Lee et al. ................. 251/149.1 |
| 2007/0083162 A1 | 4/2007 | O'Reagan et al. ........ 604/167.03 |
| 2007/0100284 A1 | 5/2007 | Leinsing et al. .......... 604/164.01 |
| 2007/0112312 A1 | 5/2007 | Fangrow ................... 604/246 |
| 2007/0112313 A1 | 5/2007 | Fangrow ................... 604/246 |
| 2007/0218757 A1 | 9/2007 | Guala ...................... 439/589 |
| 2007/0235674 A1 | 10/2007 | Vangsness et al. ........ 251/149.2 |
| 2007/0235675 A1 | 10/2007 | Kimball et al. ........... 251/149.2 |
| 2007/0235676 A1 | 10/2007 | Vangsness et al. ........ 251/149.2 |
| 2007/0238337 A1 | 10/2007 | Kimball et al. ........... 439/157 |
| 2007/0246674 A1 | 10/2007 | Kiehne .................... 251/149.6 |
| 2007/0255229 A1 | 11/2007 | Kane et al. ............... 604/248 |
| 2007/0260195 A1 | 11/2007 | Bartholomew et al. .... 604/244 |
| 2007/0270756 A1 | 11/2007 | Peppel et al. ............. 604/167.06 |
| 2008/0027398 A1 | 1/2008 | McKinnon et al. ........ 604/264 |
| 2008/0027415 A1 | 1/2008 | Isaacson et al. ........... 604/539 |
| 2008/0039802 A1 | 2/2008 | Vangsness et al. ......... 604/247 |
| 2008/0172003 A1 | 7/2008 | Plishka et al. ............ 604/249 |
| 2008/0172005 A1 | 7/2008 | Jepson .................... 604/249 |
| 2008/0190485 A1 | 8/2008 | Guala ...................... 137/1 |
| 2008/0275405 A1 | 11/2008 | Newton et al. ............ 604/256 |
| 2009/0057589 A1 | 3/2009 | Thorne, Jr. et al. ........ 251/149.1 |
| 2009/0105666 A1 | 4/2009 | Peppel .................... 604/249 |

FOREIGN PATENT DOCUMENTS

| | | | |
|---|---|---|---|
| EP | 1 243 285 A1 | 9/2002 | ............ A61M 39/02 |
| GB | 2 079 162 A | 1/1982 | ............ A62B 9/02 |
| WO | WO 83/02559 A1 | 8/1983 | ............ A61M 5/00 |
| WO | WO 93/11828 A1 | 6/1993 | ............ A61M 39/00 |
| WO | WO 96/00107 A1 | 1/1996 | ............ A61M 39/26 |
| WO | WO 97/39791 A1 | 10/1997 | ............ A61M 39/00 |
| WO | WO 98/22178 A1 | 5/1998 | ............ A61M 39/26 |
| WO | WO 98/26835 A1 | 6/1998 | ............ A61M 39/26 |
| WO | WO 98/39594 A1 | 9/1998 | ............ F16L 37/28 |
| WO | WO 00/44433 A2 | 8/2000 | ............ A61M 39/00 |
| WO | WO 01/20218 A1 | 3/2001 | ............ F16L 29/00 |
| WO | WO 03/018104 A2 | 3/2003 | ............ A61M 39/00 |
| WO | WO 03/018105 A1 | 3/2003 | ............ A61M 39/24 |
| WO | WO 2004/006046 A1 | 1/2004 | |

OTHER PUBLICATIONS

Fernand Ehrsam, Authorized Officer European Patent Office, International Search Report—Application No. PCT/US2011/041386, dated Aug. 17, 2011, together with the Written Opinion of the International Searching Authority (14 pages).

Fernand Ehrsam, Authorized Officer European Patent Office, International Preliminary Report on Patentability—Application No. PCT/US2011/041386, dated Nov. 14, 2012 (16 pages).

* cited by examiner

MEDICAL VALVE WITH FLUID VOLUME ALTERATION

FIELD OF THE INVENTION

The invention generally relates to medical valves and, more particularly, the invention relates to controlling fluid volumes within medical valves.

BACKGROUND

In general terms, medical valving devices often act as a sealed port that may be repeatedly accessed to non-invasively inject fluid into (or withdraw fluid from) a patient's vasculature. Consequently, a medical valve permits the patient's vasculature to be freely accessed without requiring such patient's skin be repeatedly pierced by a needle.

Medical personnel insert a medical instrument into the medical valve to inject fluid into (or withdraw fluid from) a patient who has an appropriately secured medical valve. Once inserted, fluid may be freely injected into or withdrawn from the patient. Problems can arise, however, when the medical instrument is withdrawn from the valve. Specifically, suction produced by the withdrawing medical instrument can undesirably cause blood to be drawn proximally into or toward the valve. In addition to coagulating and impeding the mechanical operation of the valve, blood in the valve also compromises the sterility of the valve.

SUMMARY OF THE INVENTION

In accordance with one embodiment of the present invention, a medical valve may have an open mode that permits fluid flow, and a closed mode that prevents fluid flow. The medical valve may include a housing with an inlet and an outlet, and a resilient member within the housing. The resilient member may have a body portion with a free state when undeformed by external mechanical forces, and a deformed state when the valve is in the closed mode. The body portion may be formed to radially expand to return toward the free state as the valve transitions from the closed mode to the open mode. The body portion may also define at least part of a fluid path through the valve. In some embodiments, the body portion and housing may be configured to permit the body portion to attain the free state when in the open mode. The body portion may be molded in the free state and/or may be normally biased radially outwardly in the closed mode.

In further embodiments, the resilient member may also include a proximal seal portion having a normally closed aperture therethrough. The body portion may be distal to the proximal seal portion, and may have a distal aperture through it that is biased toward an open state. The distal aperture may be closed when in the deformed state to prevent fluid flow through the valve. In some embodiments, the distal aperture may be molded open.

In still further embodiments, the valve may also include a control member that is located within the housing and contains (at least in part) the body portion (e.g., the body portion may be located within the control member). The control member may radially expand after insertion of a medical implement into the inlet, which, in turn, causes the valve to transition from the closed mode to the open mode and allows the body portion to return toward the free state. The control member may include a plurality of leg members that radially deform to expand the control member (e.g., as the valve transitions toward the open mode). The deformation of the leg members also allows the body portion to return towards the free state. 21. The leg members may bias the valve toward the closed mode. The control member may also include a biasing member (e.g., a leaf spring) that biases the valve toward to closed mode. The valve may have a substantially neutral fluid displacement at the outlet as the valve transitions from the open mode to the closed mode.

In accordance with additional embodiments, a medical valve may have an open mode that permits fluid flow, and a closed mode that prevents fluid flow. The medical valve may include a housing with an inlet and an outlet. The medical valve may also include a resilient member within the housing. The resilient member may have a proximal aperture and a distal aperture biased toward an open state to allow fluid flow through the valve when in the open mode. The resilient member may be deformed when the valve is in the closed mode to close distal aperture and prevent fluid flow through the valve. The distal aperture may return toward its open state as the valve transitions from the closed to open mode.

In some embodiments, the distal aperture may be formed to be in the open state when no radial force is applied to the resilient member. In other embodiments, the distal aperture may be molded in the open state. The distal aperture may be normally biased radially outward in the closed mode.

In additional embodiments, the medical valve may also include a control member that deforms the resilient member to close the distal aperture and prevent fluid flow through the valve when the valve is in the closed mode. The control member may radially expand as the valve transitions to the open mode to allow the distal aperture to return toward its open state, and allow fluid flow through the valve. The control member may include a plurality of leg members that radially deform to expand the control member as the valve transitions toward the open mode. The leg members may bias the valve toward the closed mode. The control member may also include a biasing member (e.g., a leaf spring) that biases the valve toward to closed mode.

In some embodiments, the resilient member may include a body portion and a proximal seal portion. The body portion has a free state when undeformed by external mechanical forces, and a deformed state when the valve is in the closed mode. The body portion may be formed to return toward the free state as the valve transitions from the closed mode to the open mode. The body portion may define at least part of a fluid path through the valve, and may be distal to the proximal seal portion. The distal aperture may be located within the body portion and the proximal aperture may be located within the proximal seal portion.

In further embodiments, the body portion may have an outer dimension that is at its natural dimension when in the free state. The control member may deform the body portion such that the outer dimension expands past the natural dimension when the valve is in the open mode.

In accordance with additional embodiments, a method may include connecting a medical valve to a patient, inserting a medical implement through a valve inlet, moving the medical implement distally within the housing to transition the valve from a closed mode to an open mode, and transferring fluid between the medical implement and the patient through the valve. The medical valve may include a housing having the inlet and an outlet, a resilient member, and a control member. The resilient member may be within the housing and have a proximal aperture and a distal aperture biased toward an open state. The control member may deform the resilient member to close the distal aperture when the valve is in a closed mode. Distal movement of the medical implement may cause the control member to expand generally radially to allow the distal aperture to return toward the open state.

The distal aperture may be formed to be in the open state when no radial force is applied to the resilient member and/or may be normally biased radially outward in the closed mode. The control member may also include a plurality of leg members that radially deform to expand the control member as the valve transitions toward the open mode. Additionally, the control member may include a biasing member that biases the valve toward to closed mode.

In accordance with further embodiments, a resilient member for a medical valve having a housing with an inlet and an outlet may include a proximal seal portion and a body portion. The body portion may be distal to the proximal seal portion and have a free/at-rest state when the valve is in the open mode. The body portion may also have a compressed state when the valve is in the closed mode. The body portion may be molded in the free/at-rest state and return to the at-rest state as the valve transitions from the closed mode to the open mode.

BRIEF DESCRIPTION OF THE DRAWINGS

The foregoing features of the invention will be more readily understood by reference to the following detailed description, taken with reference to the accompanying drawings, in which.

DESCRIPTION OF ILLUSTRATIVE EMBODIMENTS

In illustrative embodiments, a medical valve has an internal valve mechanism with a resilient member having a normally open distal aperture. The medical valve may also have a control member that compresses the resilient member to close the distal aperture when the valve is in the closed mode. Other embodiments of a medical valve have an internal resilient member with a normally outwardly biased body portion. Actuation of this valve urges the resilient member toward its free state. Details of illustrative embodiments are discussed below.

Figure 1:
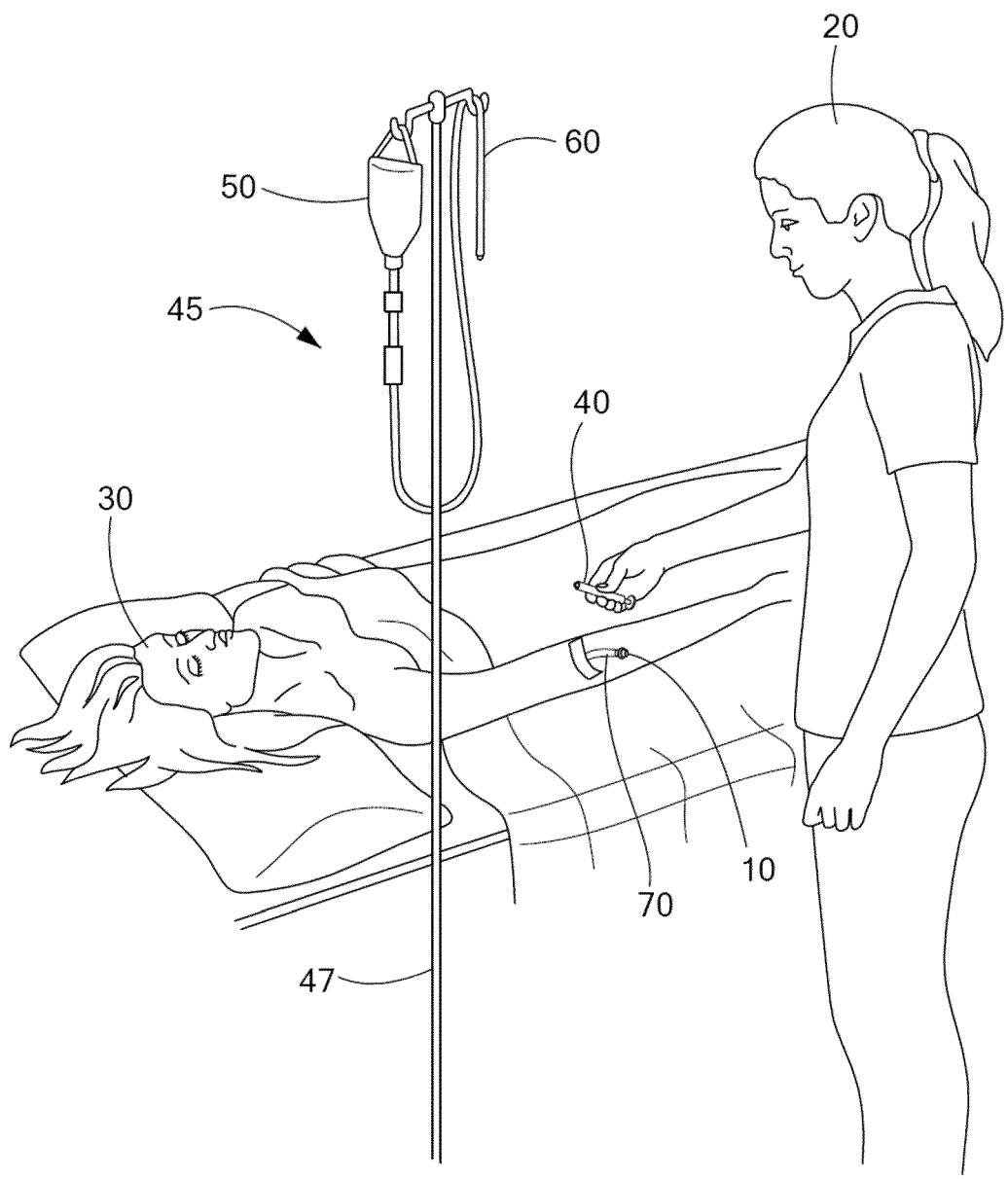
FIG. 1 schematically shows one use of a medical valve configured in accordance with one embodiment of the present invention.

FIG. 1 schematically shows one illustrative use of a medical valve 10 configured in accordance with illustrative embodiments of the invention. In this example, a catheter 70 connects the valve 10 with a patient's vein (the patient is identified by reference number 30). Adhesive tape or similar material may be coupled with the catheter 70 and patient's arm to ensure that the valve 10 remains in place.

After the valve 10 is in place, a nurse, doctor, technician, practitioner, or other user (schematically identified by reference number 20) may intravenously deliver medication to the patient 30, who is lying in a hospital bed. To that end, before the valve 10 is properly primed and flushed (e.g., with a saline flush), the nurse 20 swabs the top surface of the valve 10 to remove contaminants. Next, the nurse 20, once again, swabs the top surface of the valve 10 and uses a medical instrument 40 (e.g., a syringe having a distally located blunt, luer tip complying with ANSI/ISO standards) to inject medication into the patient 30 through the valve 10. For example, the medical practitioner 20 may use the valve 10 to inject drugs such as heparin, antibiotic, pain medication, other intravenous medication, or other fluid deemed medically appropriate. Alternatively, the nurse 20 (or other user) may withdraw blood from the patient 30 through the valve 10.

The medical valve 10 may receive medication or other fluids from other means, such as through a gravity feed system 45. In general, traditional gravity feeding systems 45 often have a bag 50 (or bottle) containing a fluid (e.g., anesthesia medication) to be introduced into the patient 30. The bag 50 (or bottle) typically hangs from a pole 47 to allow for gravity feeding. The medical practitioner 20 then connects the bag/bottle 50 to the medical valve 10 using tubing 60 having an attached blunt tip. In illustrative embodiments, the blunt tip of the tubing has a luer taper that complies with the ANSI/ISO standard.

After the tubing 60 is connected to the medical valve 10, gravity (or a pump) causes the fluid to begin flowing into the patient 30. In some embodiments, the feeding system 45 may include additional shut-off valves on the tubing 60 (e.g., stop-cock valves or clamps) to stop fluid flow without having to disconnect the tubing 60 from the valve 10. Accordingly, the valve 10 can be used in long-term "indwell" procedures.

After administering or withdrawing fluid from the patient 30, the nurse 20 should appropriately swab and flush the valve 10 and catheter 70 to remove contaminants and ensure proper operation. As known by those skilled in the art, there is a generally accepted valve swabbing and flushing protocol that should mitigate the likelihood of infection. Among other things, as summarized above, this protocol requires proper flushing and swabbing before and after the valve 10 is used to deliver fluid to, or withdraw fluid from the patient 30.

Figure 2A:
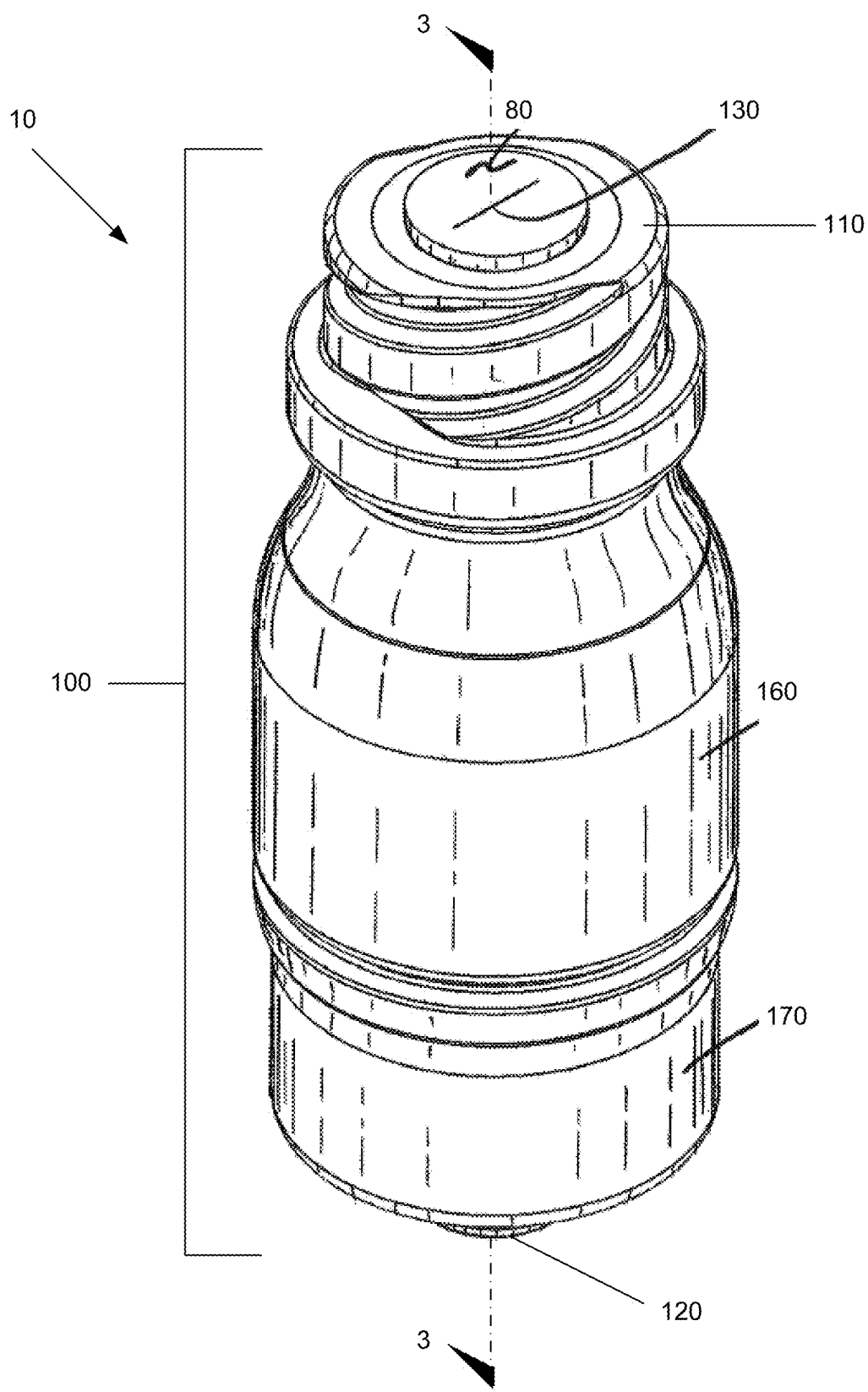
FIG. 2A schematically shows a perspective view of a medical valve configured in accordance with illustrative embodiments of the present invention.
Figure 2B:
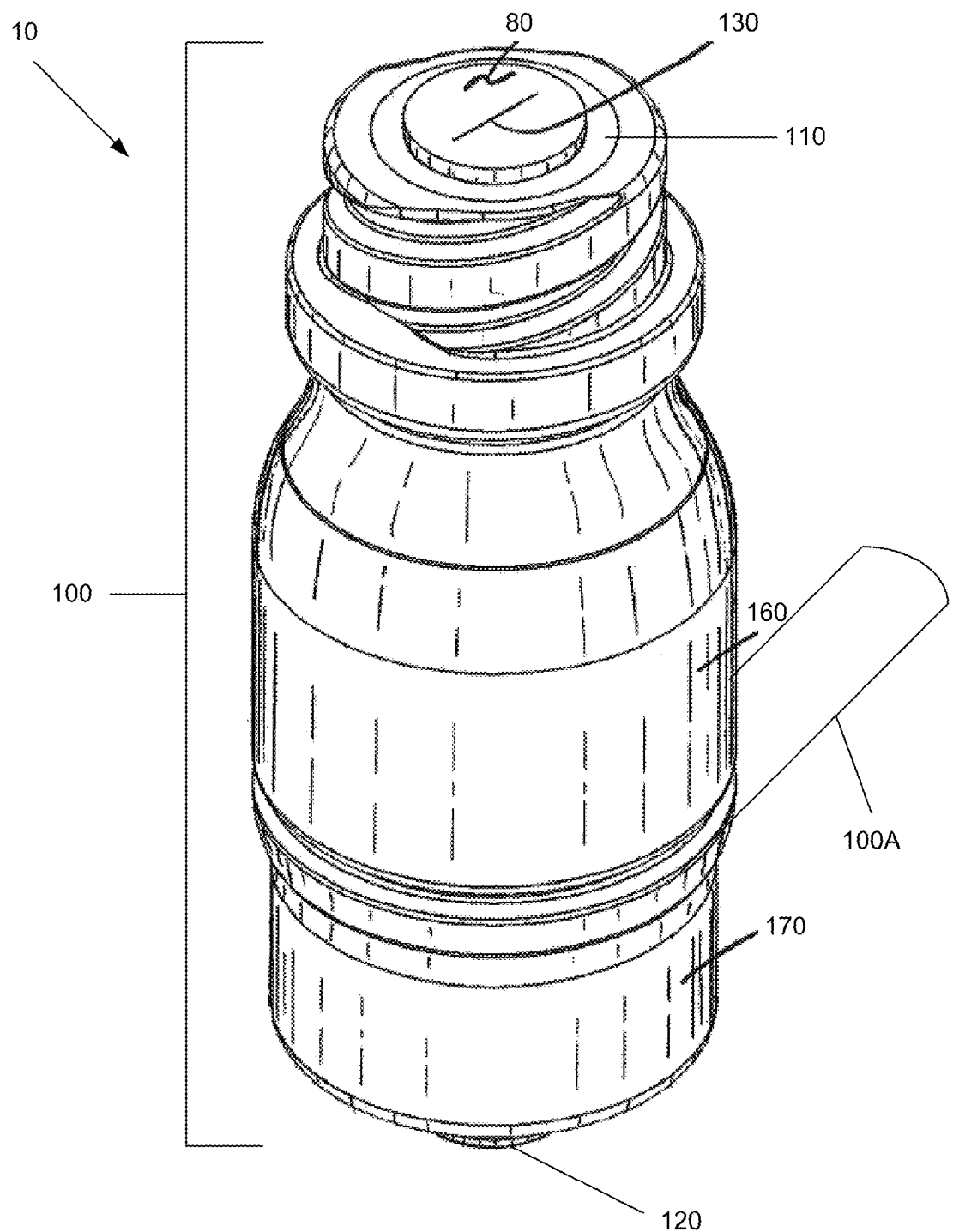
FIG. 2B schematically shows a perspective view of a medical valve of FIG. 2A with a Y-site branch.

FIG. 2A schematically shows a perspective view of the medical valve 10 shown in FIG. 1, while FIG. 2B schematically shows the same valve with a Y-site branch 100A. In illustrative embodiments, during withdrawal of the instrument 40, the valve 10 may be configured to have a substantially positive fluid displacement or a substantially neutral fluid displacement (between about plus or minus 1 microliter of fluid displacement, discussed below). In other words, withdrawal of a medical instrument 40 causes either a positive fluid displacement or essentially no or negligible fluid displacement at the distal end of the valve 10.

In this context, fluid displacement generally refers to the flow of fluid through the distal port 120 of the valve 10 (discussed below). Accordingly, a positive fluid displacement generally refers to fluid flowing in a distal direction through the distal port 120, while a negative fluid displacement generally refers to a fluid flowing in a proximal direction through the distal port 120. Of course, not all embodiments exhibit this quality. For example, in alternative embodiments, the valve 10 may have a neutral fluid displacement when the instrument 40 is withdrawn.

It should be noted that the fluid displacements discussed herein refer to the "net" fluid displaced through the distal port 120 (i.e., upon insertion or withdrawal of an instrument 40 only-not including when the instrument 40 actually injects fluid through the valve). Specifically, during insertion or withdrawal of the instrument 40, the actual flow of fluid through the distal port 120 may change direction and thus, fluctuate. However, when considering this fluctuation, the net change in fluid flow through the distal port 120 should be 1) positive when the valve exhibits a "positive fluid displacement," and 2) negative when the valve exhibits a "negative fluid displacement." In a similar manner, a substantially neutral fluid displacement occurs when, as noted above, the valve 10 has a net fluid displacement of between about plus or minus one microliter. Of course, the fluid displacement of the valve 10 is discussed herein in terms of one stroke of the instrument 40 (i.e., insertion or withdrawal of the instrument 40).

Ideally, a valve with a neutral displacement has 0.0 microliters of positive or negative fluid displacement. As suggested above, however, in practice, a neutral displacement actually can have a very slight positive or negative displacement (e.g., caused by a manufacturing tolerance), such as a displacement on the order of positive or negative one microliter, or less. In other words, in such embodiments, the volumes of fluid forced through the distal port 120 in a neutral displacement valve are negligible (ideally zero microliters) and should have a negligible impact on the goals of the valve.

Some embodiments may have a very low positive or negative fluid displacement upon withdrawal. For example, such valves may have a negative fluid displacement of about one to two microliters (i.e., about one to two microliters of fluid drawback, which is proximally directed), or about one to two microliters positive fluid displacement (i.e., about one to two microliters of positively pushed fluid, which is distally directed). Although such amounts are in the positive or negative fluid displacement ranges, they still should represent a significant improvement over valves that exhibit higher positive or negative fluid displacements upon withdrawal.

The neutral, positive, or negative fluid displacement of a valve may be corrupted by manual handling of the valve 10, catheter 70 or the instrument 40 during the fluid transfer. For example, a slight inward force applied to the shaft of the medical instrument 40 (e.g., by the nurse's hand when simply holding the medical instrument 40) can have the effect of adding a positive fluid displacement from the medical instrument 40 (when the force is applied) and, ultimately, through the valve 10. In fact, releasing this force from the medical instrument 40 actually may draw fluid proximally, causing a negative fluid displacement that further corrupts fluid displacement. These effects, however, should not be considered when determining the nature of fluid displacement through the distal port 120. To overcome the problem noted above with regard to squeezing the medical instrument shaft, for example, the nurse 20 can hold another part of the medical instrument that does not contain the fluid (e.g., stubs at the proximal end of the medical instrument 40).

To accomplish these desired goals, the valve 10 has a housing 100 forming an interior having a proximal port 110 for receiving the instrument 40, and the noted distal port 120 having the discussed fluid displacement properties. The valve 10 has an open mode that permits fluid flow through the valve 10, and a closed mode that prevents fluid flow through the valve 10. To that end, the interior contains a valve mechanism that selectively controls (i.e., allow/permits) fluid flow through the valve 10. The fluid passes through a complete fluid path that extends between the proximal port 110 and the distal port 120.

It should be noted that although much of the discussion herein refers to the proximal port 110 as an inlet, and the distal port 120 as an outlet, the proximal and distal ports 110 and 120 also may be respectively used as outlet and inlet ports. Discussion of these ports in either configuration therefore is for illustrative purposes only.

The valve 10 is considered to provide a low pressure seal at its proximal end 110. To that end, the proximal end 110 of the medical valve 10 has a resilient proximal seal 80 with a resealable aperture 130 that extends entirely through its profile. The aperture 130 may, for example, be a pierced hole or a slit. Alternatively, the proximal seal 80 may be molded with the aperture 130. To help center the proximal seal 80 within the proximal port 110 and keep the aperture 130 closed (e.g., by pre-loading the aperture 130), the proximal gland may have centering ribs 82 nearer the proximal end of the proximal seal 80.

As mentioned above, some embodiments of the present invention may be swabbable. To that end, the proximal seal 80 may be substantially flush with or extend slightly proximal to the proximal port 110 when the valve 10 is in the closed mode. This creates a swabbable surface at the inlet of the valve 10 and allows the nurse 20 to perform the swabbing protocol discussed above.

Figure 3A:
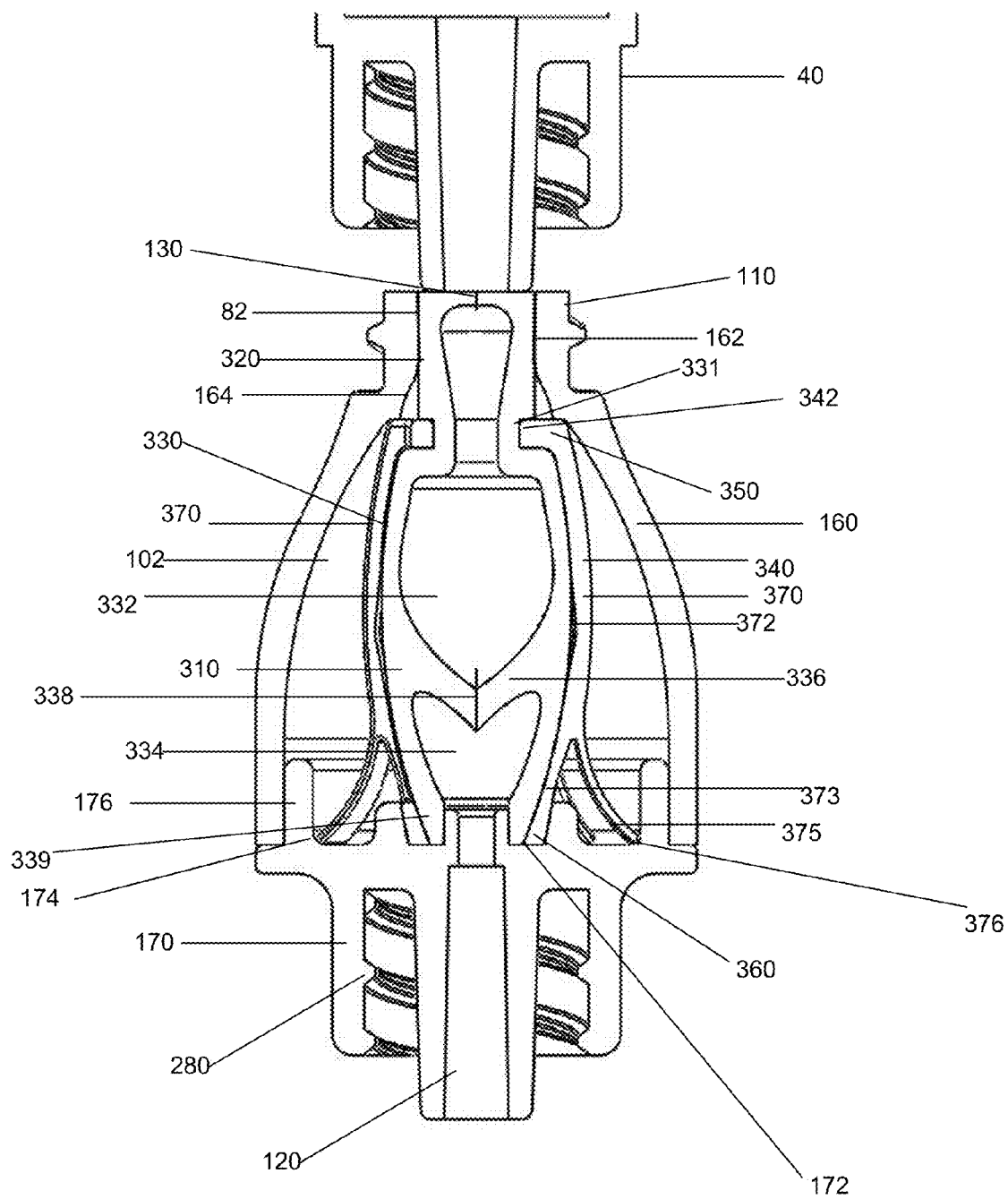
FIG. 3A schematically shows a cross-sectional view of the valve shown in FIG. 2A in the closed mode along line 3-3.
Figure 3B:
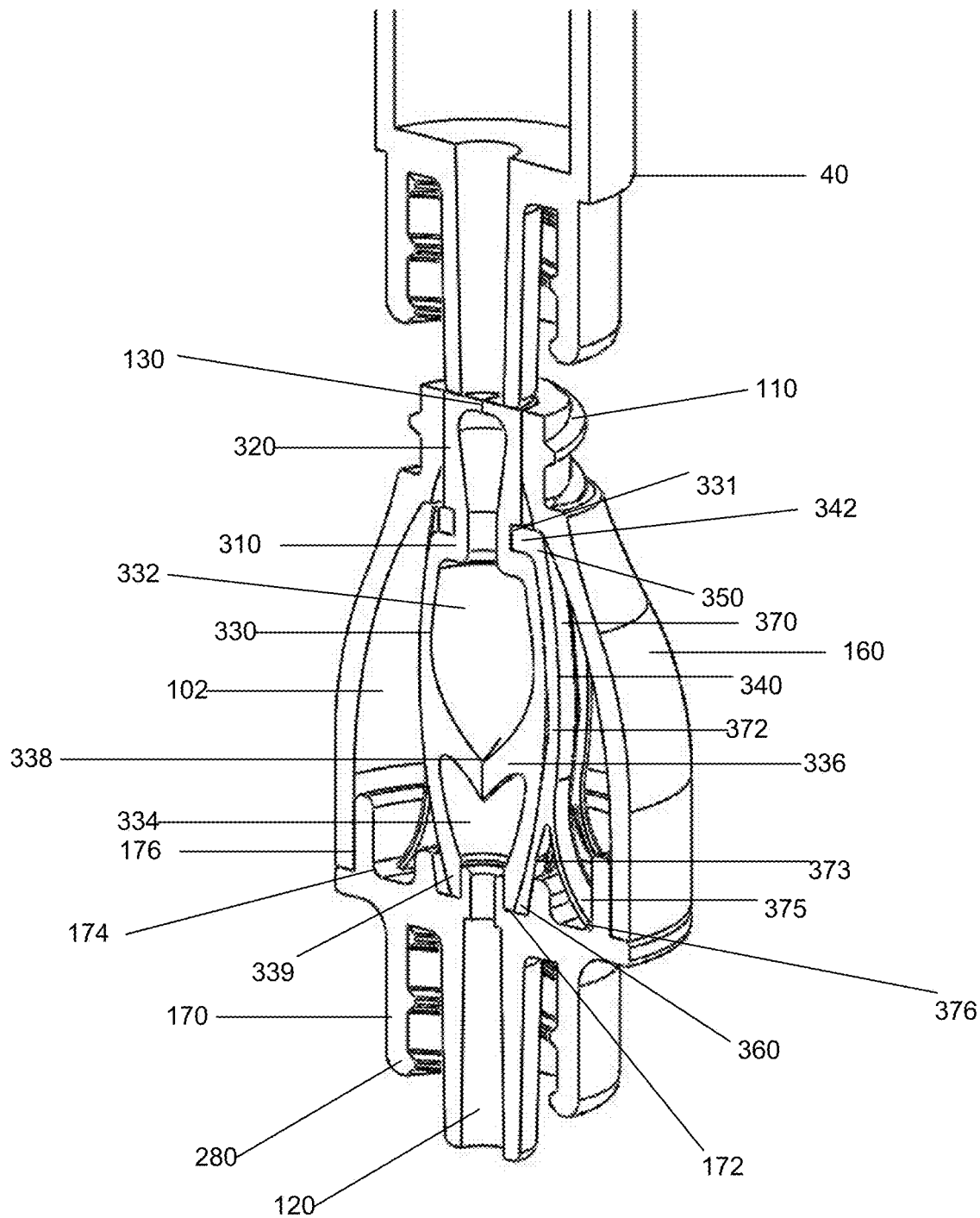
FIG. 3B schematically shows an angled cross-sectional view of the valve shown in FIG. 2A in the closed mode along line 3-3.

FIG. 3A schematically shows the cross section of the valve shown in FIG. 2A along the line 3-3. FIG. 3B schematically shows an angled/perspective view of the cross section shown in FIG. 3A. FIGS. 3A and 3B show the valve 10 in the closed position when no medical instrument or other instrument is inserted through the proximal port 110. As shown, the housing 100 includes an inlet housing 160 and an outlet housing 170, which connect together to form the interior of the medical valve 10. Within the interior, the medical valve 10 has a valve mechanism. The inlet housing 160 and the outlet housing 170 may be joined together in a variety of ways, including a snap-fit connection, ultrasonic welding, plastic welding, or other method conventionally used in the art.

The internal valve mechanism may include a resilient member 310 at least partly within a control member 340 that cooperate with one another to selectively open and close the valve 10. In the embodiment shown in FIGS. 3A and 3B, the resilient member 310 is typically formed from a resilient material that allows it to easily deform (e.g., silicone). As discussed in greater detail below, the control member 340 may be formed from a resilient material that is more rigid (i.e. greater flexural modulus) than the resilient member 310, yet still allows some deformation. Details of the valve operation, including the interaction between the control member 340 and the resilient member 310 are discussed in greater detail below, with respect to FIGS. 4A and 4B.

As shown in FIGS. 3A and 3B, the resilient member 310 has a proximal portion 320 and a distal portion 330 (e.g., a body portion). The proximal portion may include the low pressure seal described above. For example, the proximal portion 320 includes the proximal seal 80 with its resealable aperture 130. At least a portion of the proximal portion 320 may be located within the proximal port 110 to keep the aperture 130 closed (e.g., by pre-loading), as described above.

The body portion 330 is distal to the proximal portion 320 and extends into a wider cavity 102 within the housing 100. The body portion 330 in this embodiment thus may be considered to include a proximal volume 332 and a distal volume 334 separated by a distal seal 336. Like the proximal seal 80, the distal seal 336 may also have a distal aperture 338 extending through it. As discussed in greater detail below, when the valve 10 is in the open mode, the proximal aperture 130 and the distal aperture 338 are open to allow fluid flow to pass through the valve 10.

Figure 5:
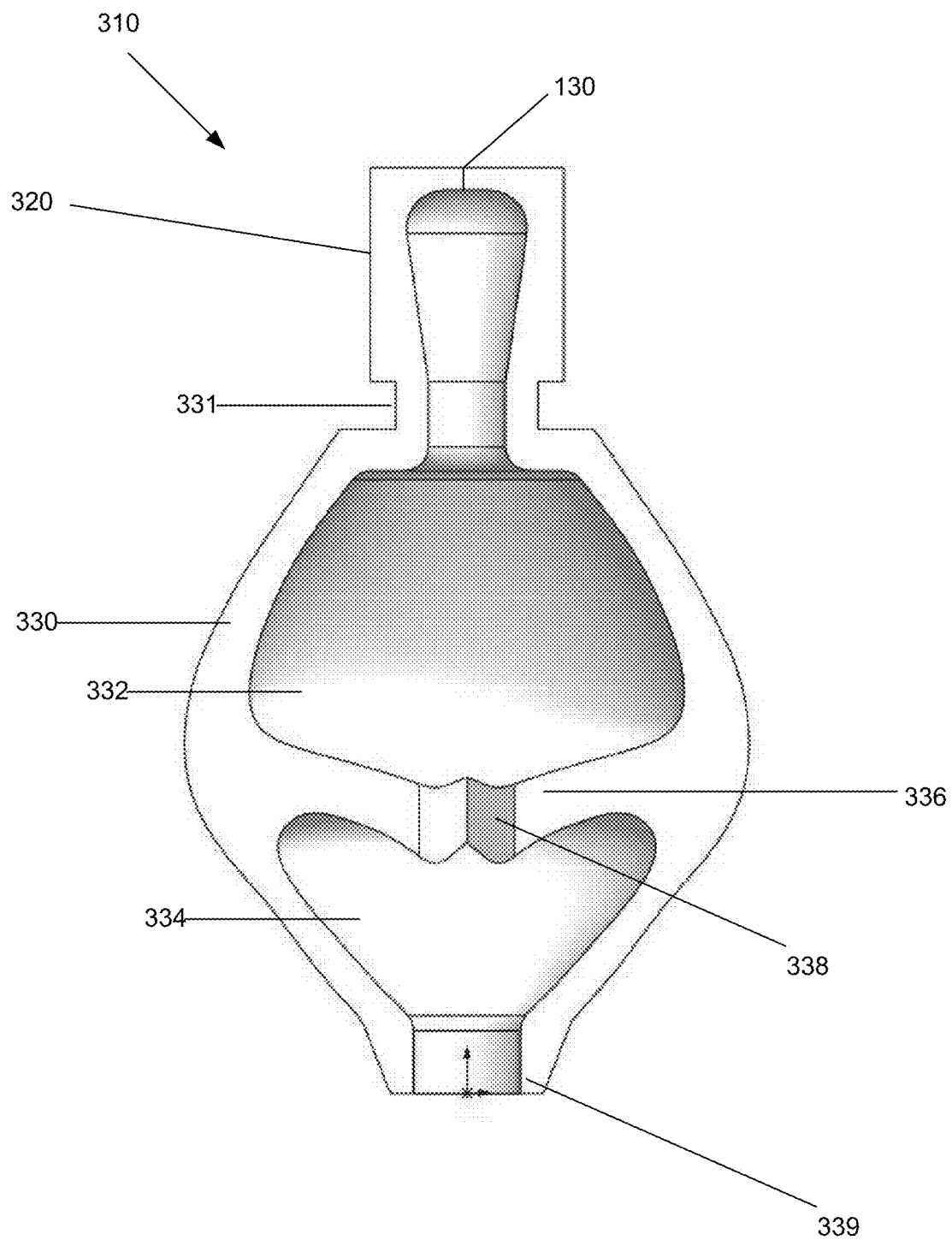
FIG. 5 schematically shows a cross-sectional view of the resilient member within the valve shown in FIG. 2A in the free/at-rest state.

As shown in FIG. 5, the resilient member 310 can be formed and/or molded such that the distal seal aperture 338 is normally in the open position. In other words, when the resilient member 310 is in the free/at-rest/undeformed state (e.g., the state at which the resilient member is not exposed to any external mechanical forces), the distal seal aperture 338 will be open. For example, the resilient member 310 is in its free state before assembly—when the resilient member 310 is an independent component prior to insertion into the control member 340. Additionally, when in the free state, the outer dimension of the body portion 330 will be at its maximum natural dimension.

Accordingly, as described in greater detail below, when the valve 10 is in the closed mode, the control member 340 deforms the body portion 330 to close the distal seal aperture 338 (and compress/reduce the outer dimension). Thus, when in the closed mode, the body portion 330 and distal seal aperture 338 are biased radially outward; namely, they normally apply a generally radially outward force that the control member 340 controls. Thus, expansion and contraction of the control member 340 controls the movement of the body portion 330 of the resilient member 310.

Returning to FIGS. 3A and 3B, the resilient member 310 may also include an external groove 331 between the proximal portion 320 and the body portion 330. As discussed in greater detail below, the external groove 331 may receive a flange 342 located on the control member 340 to secure the control member 340 to the resilient member 310. Additionally, the resilient member 310 may also have a flanged portion 339 at the distal end of the body portion 330. This flanged portion 339 may be captured within a recess 172 in the outlet housing 170 to secure the resilient member 310 within the housing 100.

Figure 6:
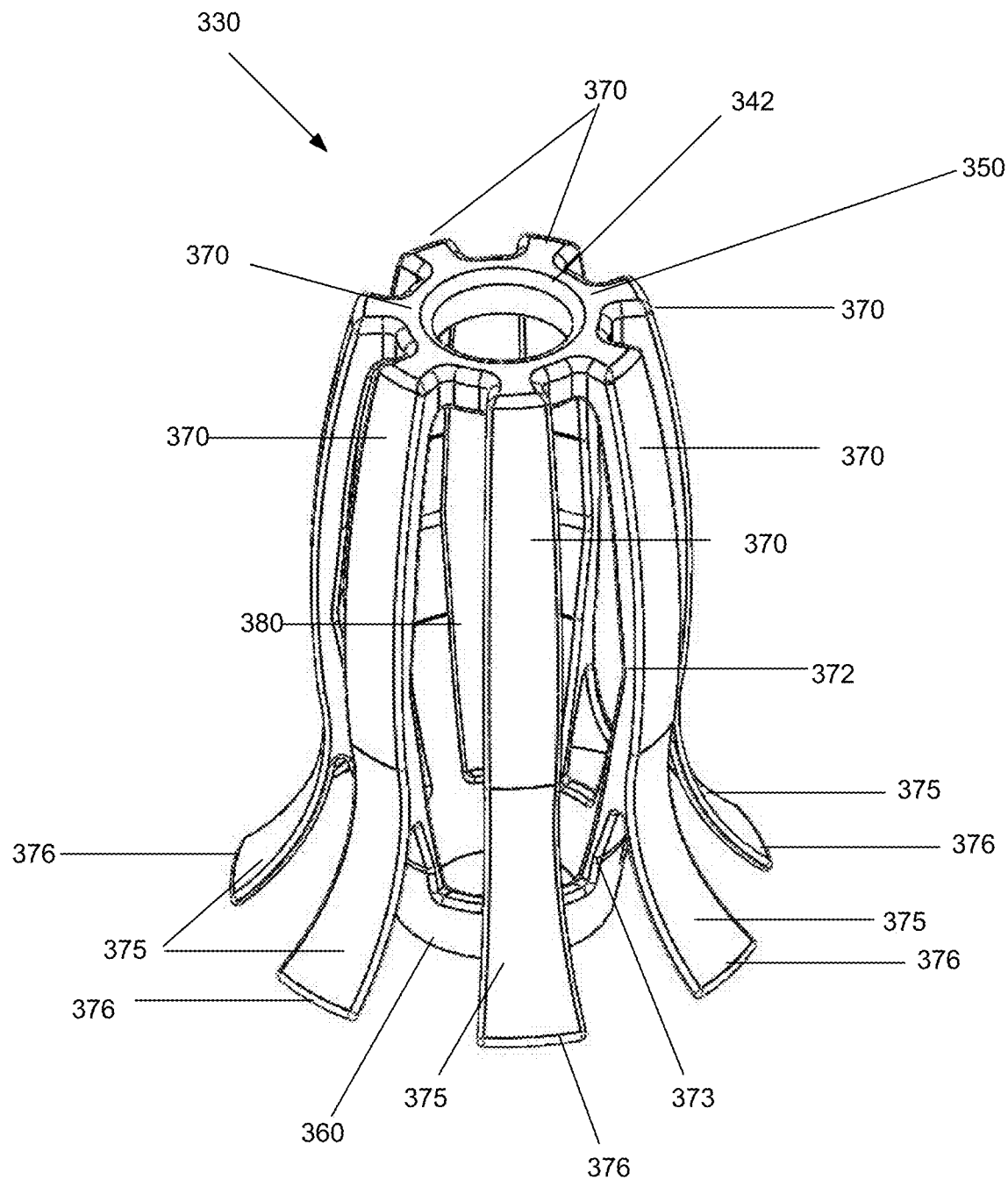
FIG. 6 schematically shows a perspective view of the control member within the valve shown in FIG. 2A in the free/at rest-state.

FIG. 6 shows additional details of the control member 340, which may substantially surround the resilient member 310 (e.g., the resilient member 310 may be located, at least in part, within the control member 340) and, as discussed in greater detail below, control the deformation of the resilient member 310. In particular, as best shown in FIG. 6, the control member 340 may include a top ring 350, a bottom ring 360 and a plurality of leg members 370 extending between the top ring 350 and the bottom ring 360. The top ring 350, bottom ring 360, and the leg members 370 together define the structure of the control member 340 and create an internal cavity 380 in which the resilient member 310 (e.g., the body portion 330) may be located. Like the flanged portion 339 of the resilient member, a portion of the bottom ring 360 may be captured within the recess 172 in the outlet housing 170 to secure the control member 340 within the housing 100.

As discussed above, the control member 340 controls the deformation and compression of the resilient member 310 and substantially deforms the resilient member 310 when the valve 10 is in the closed mode. To that end, the control member 340 should be formed from a material that is more rigid than that of the resilient member 310. However, because the control member 340 must deform to allow the valve 10 to transition between the open and closed modes, the control member material must also be resilient. For example, the control member 340 may be made from a resilient plastic (e.g. soft thermoplastic) that allows the leg members 370 to deform/flex as the valve 10 opens, and return to their at rest state as the valve 10 closes. Alternatively, the control member 340 may be made from a resilient metal (e.g. nitinol) to enable return of the leg members 370 to their at rest state.

Unlike the resilient member 310, the control member 340 is generally in its free/at-rest state (shown in FIG. 6) when the valve 10 is in the closed mode. Therefore, as discussed in greater detail below, as the valve 10 transitions from the closed mode to the open mode, the control member 340 expands/deforms to the state shown in FIG. 7. Furthermore, as the valve 10 returns to the closed mode, the control member 340 returns to its at rest state (e.g., as shown in FIG. 6).

Figure 7:
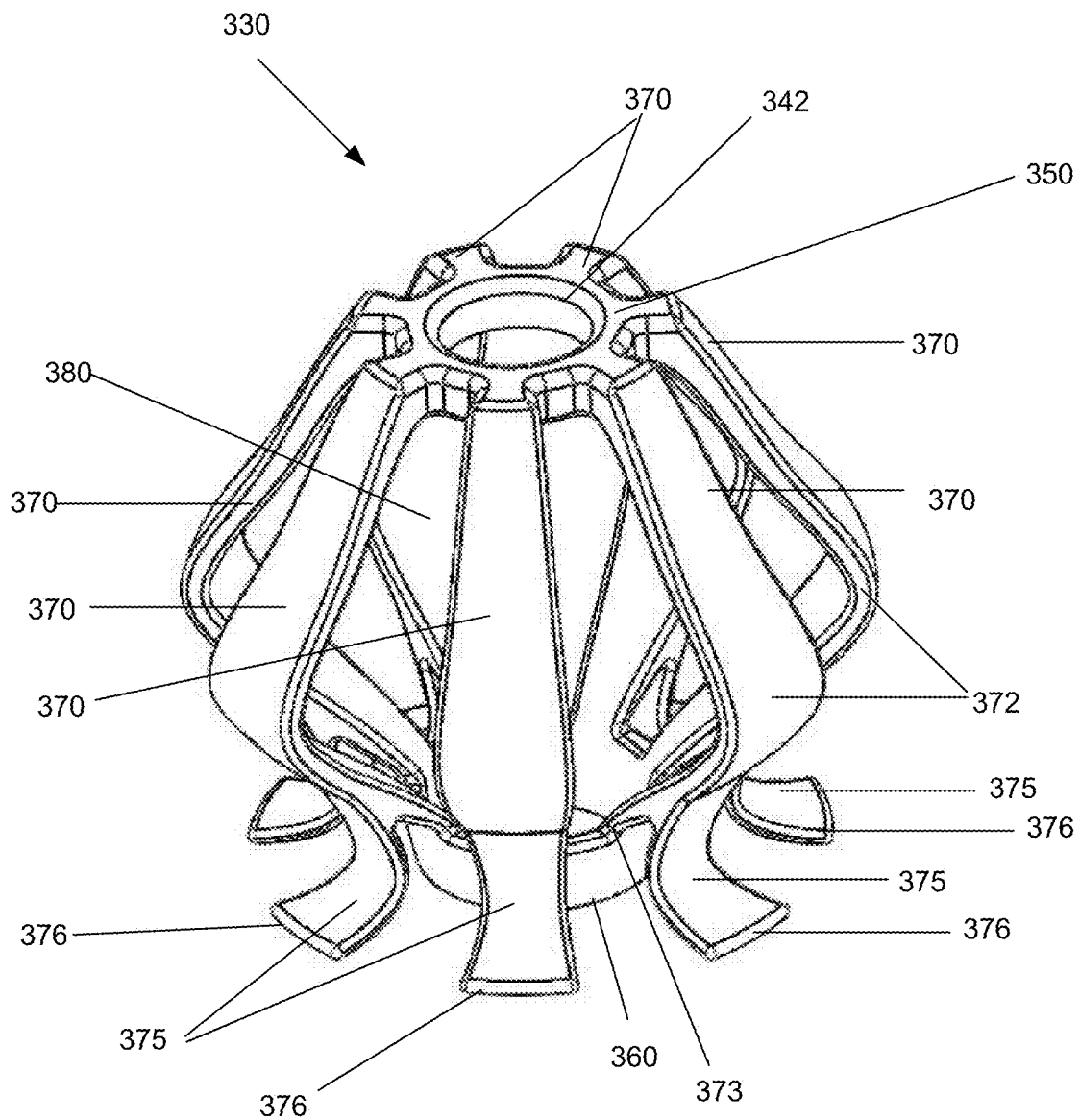
FIG. 7 schematically shows a perspective view of the control member within the valve shown in FIG. 2A in the deformed state.

As discussed above, as the medical valve 10 transitions between the open and closed modes, the leg members 370 may deform and bow outwardly (see FIG. 7). To that end, the leg members 370 may have varying thicknesses along their length, and may have one or more thinned portions. For example, the leg members 370 may have a first thinned portion 372 near the middle of the leg member 370 and a second thinned portion 373 near the bottom of the leg member 370. These thinned portions 372/373 allow the leg members 370 to flex/bend more easily as the valve 10 transitions between the open and closed modes. Additionally, the thinned portions 372/373 also help the leg members 370 flex/bend consistently each time the valve 10 is opened/closed (e.g., the leg members 350 will primarily bend at the thinned portions 372/373).

Additionally, to help the control member 340 return to its normal state (e.g., the state shown in FIG. 6) when the valve 10 closes, the control member 340 may also include spring members 375 that bias the control member 340 toward its free/at-rest state and the valve 10 toward the closed mode. For example, each of the leg members 370 may include a leaf spring 375 extending from it. The ends 376 of the leaf springs 375 may contact the base 174 of an upward protrusion 176 on the outlet housing 170. As the valve 10 transitions from the closed mode to the open mode, the leaf springs 375 will compress/deform as the control member 340 deforms. As the valve 10 transitions from the open mode to the closed mode, the leaf springs 357 will bias the valve 10 toward the closed mode (e.g., by biasing the control member 340 back to the at-rest position).

As mentioned above and as illustrated in FIGS. 4A and 4B, deformation of the control member 340 opens the valve 10. In particular, when a medical practitioner or other user inserts a medical implement 40 into the valve, the proximal portion 320 of the resilient member 310 begins to deform and move distally within the proximal housing 160. As the proximal portion 320 continues to deform and move distally, the proximal aperture 130 will open and allow fluid to flow into the body portion proximal volume 332. It is important to note that in the embodiment shown, the proximal seal aperture 130 is expected to remain closed until the proximal seal 80 exits the luer taper region 162 of the inlet housing 160 and enters the expansion region 164. As the proximal seal 80 enters the expansion region 164, the proximal seal aperture 130 will open.

Upon further distal movement of the medical instrument 40 into the valve 10, the force of the distal movement of the medical instrument 40 will be translated to the control member 340, which will begin to deform, as described above. For example, the leg members 370 will begin to deform and bow/flex outwardly at the thinned portions 372/373. Additionally, the leaf springs 375 will also begin to deform, as described above.

As mentioned above, the resilient member 310 is formed/molded such that when it is in the free state shown in FIG. 5, the distal aperture 338 is in the open position (e.g., the distal aperture 338 is normally open), and the outer dimension of the body portion 330 is at its maximum natural dimension. Additionally, when the valve 10 is in the closed mode, the control member 340 compresses/deforms the body portion 330 of the resilient member 310 and closes the distal aperture 338 to prevent fluid flow through the valve 10. As the valve transitions from the closed mode to the open mode and the leg members 370 begin to deform/flex outwardly, the force applied to the resilient member 310 by the control member 340 is reduced and/or removed and the resilient member 310 will begin to return toward its free/at-rest state (e.g., the state in which no forces are applied to the resilient member 310, as shown, in FIG. 5).

Figure 4A:
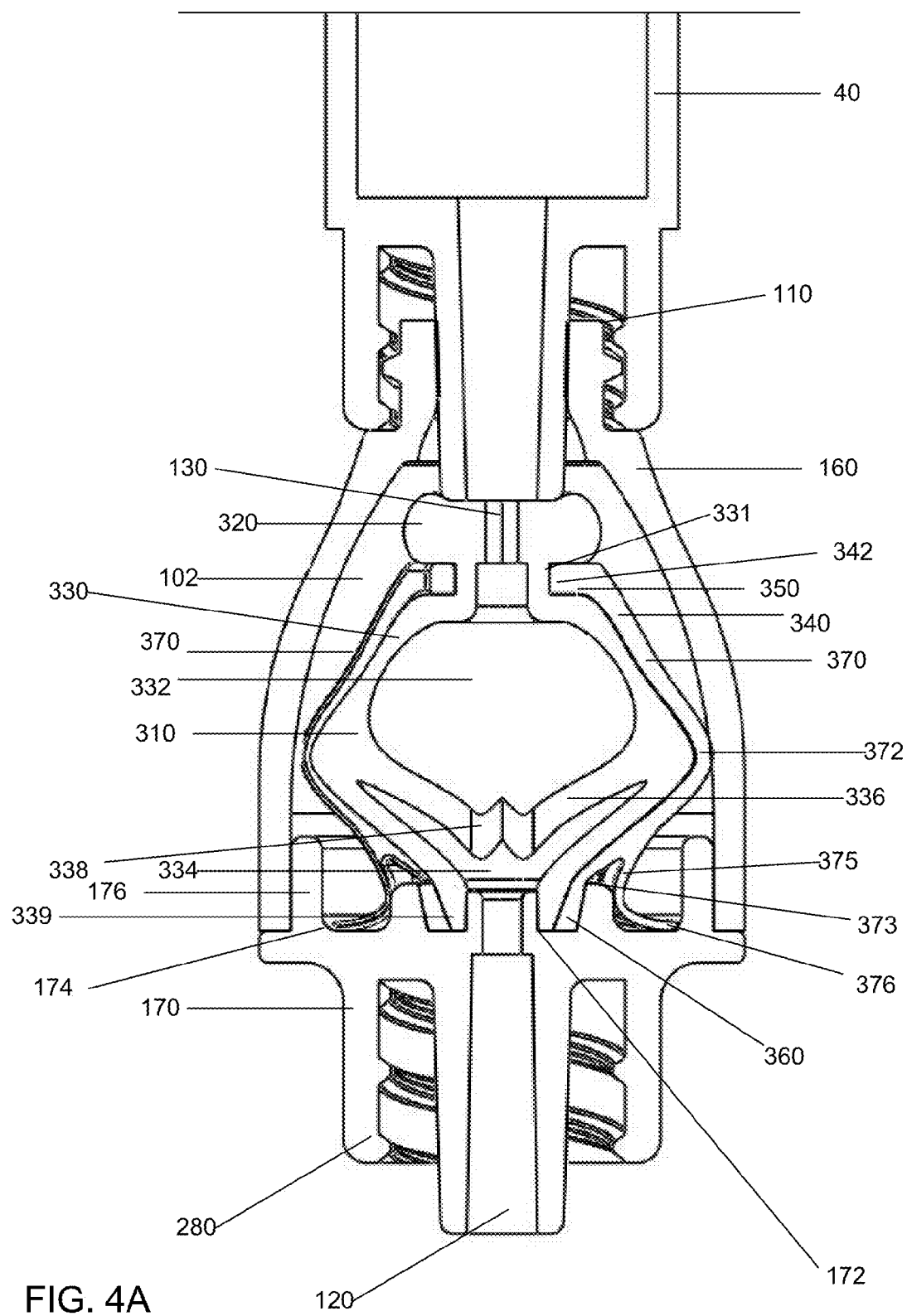
FIG. 4A schematically shows a cross-sectional view of the valve shown in FIG. 2A in the open mode along line 3-3.
Figure 4B:
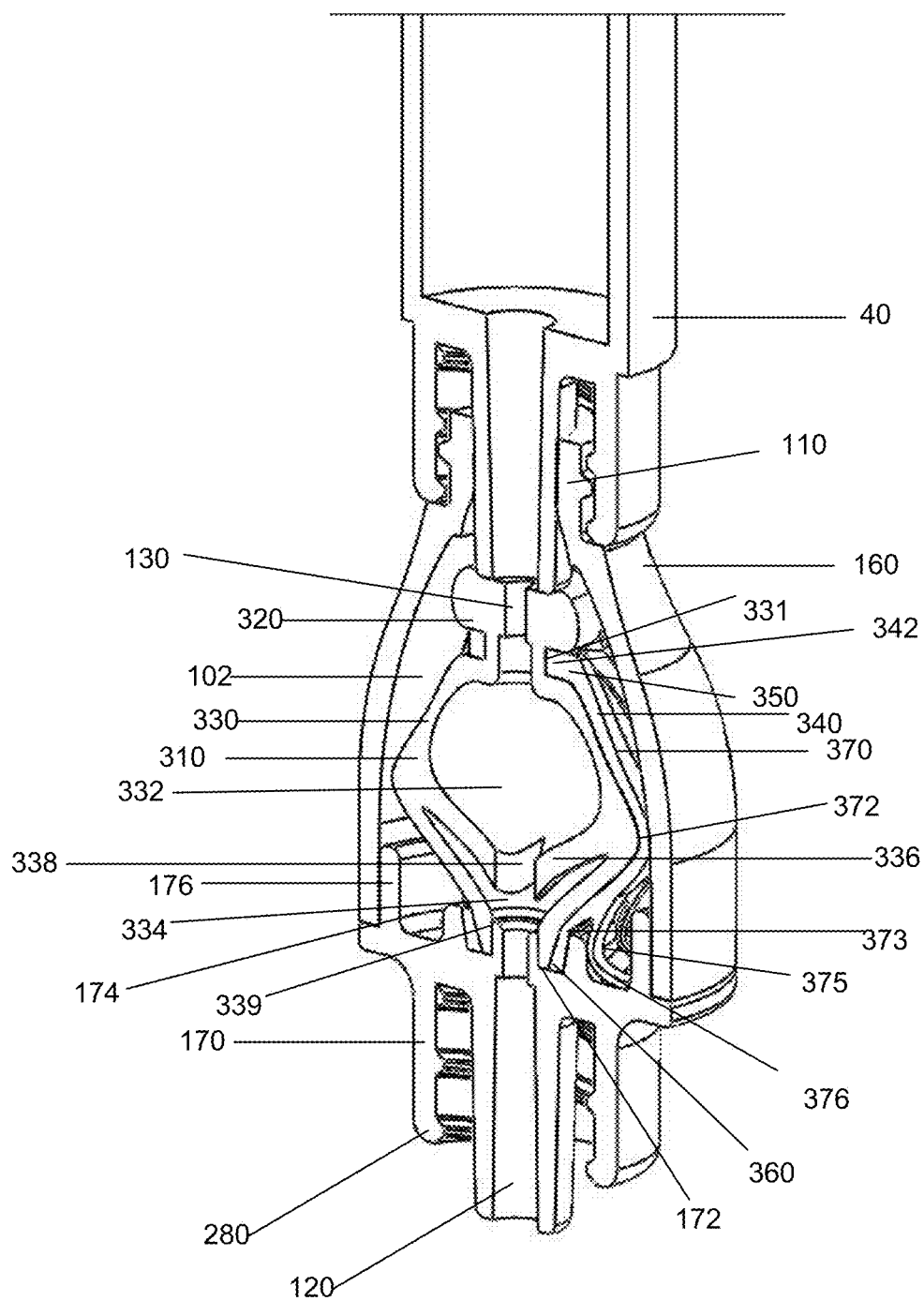
FIG. 4B schematically shows an angled cross-sectional view of the valve shown in FIG. 2A in the open mode along line 3-3.

As the resilient member 310 begins to return toward the free state, the distal aperture 338, in turn, begins to open to fluidly connect the valve inlet 110 and outlet 120. Once the valve 10 is in the open mode (e.g., after the distal seal aperture 338 is open), the medical practitioner 20 or other user may transfer fluid to and/or from the patient 30. When fluid is transferred to and/or from the patient 30, the fluid passes through a fluid path within the valve 10. As the name suggests, the fluid path is the path the fluid takes as it passes through the valve 10. As shown in FIGS. 4A and 4B, the fluid path includes the proximal aperture 130, the proximal volume 332, the distal seal aperture 338, and the distal volume 334.

It is important to note that, in some embodiments, the resilient member 310 (e.g., the body portion 330) does not need to fully return to its free/at-rest state for the valve 10 to be in the open mode. Rather, the control member 340 and the resilient member 310 may be configured such that the control member 340 still applies some compressive force on the resilient member 310 when the valve 10 is in the fully open mode. In such embodiments, the distal seal aperture 338 may, or may not fully open and the resilient member 310 may not return to the free/at-rest state shown in FIG. 5 (e.g., the outer dimension may not be at its maximum natural dimension). However, in such embodiments, the control member 340 must expand enough to remove enough compressive force to allow the distal seal aperture 338 to open sufficiently to achieve the desired flow through the valve 10.

Conversely, in some embodiments, the body portion 330 may be deformed such that the outer dimension extends beyond its natural maximum dimension (e.g., the maximum dimension in the free state) when the valve 10 is in the open mode. In such embodiments, the control member 340 may continue to expand radially outward after the body portion 330 reaches its free state (e.g., if the medical implement 40 is inserted further). The additional radial expansion of the control member 340 will, in turn, apply a longitudinal force on the body portion 330 (e.g., as the length of the control member 340 decreases) and cause the outer dimension of the body portion 330 to expand radially outwardly past its maximum natural dimension.

Upon disconnection and withdrawal of the medical implement 40, the leaf springs 375 and the leg members 370 urge the valve 10 from the open mode shown in FIGS. 4A and 4B back toward the closed mode shown in FIGS. 3A and 3B. In particular, as the leaf springs 375 and the leg members 370 return to their position/states shown in FIGS. 3A and 3B, they will urge the control member 340 back to its at-rest state (e.g., as shown in FIGS. 3A, 3B, and 6). The control member 340 will then, in turn, begin to deform/compress the body portion 330 of the resilient member and close the distal aperture 338. Additionally the proximal portion 320 of the resilient member 310 will enter the luer taper region 162 and the proximal aperture 130 will close. It is important to note that the control member 340 does not need to fully return to its free/at-rest state for the valve 10 to be in the closed mode.

As mentioned above, various embodiments of the present invention may have differing fluid displacements at the outlet 120 upon insertion and withdrawal of the medical implement. For example, the valve 10 may have a positive, negative, or a neutral fluid displacement at the outlet 120 upon withdrawal of the medical implement. To that end, valve designers/engineers may "tune" various embodiments of the valve 10 to achieve the desired fluid displacement. In particular, the fluid displacement at the outlet is dependent upon, among other things, the original state (e.g., the free/at-rest/as-molded state) of the resilient member 310 and the respective sizes of the body portion proximal volume 332 and distal volume 334. Therefore, to create a positive fluid displacement at the outlet 120, the resilient member 310 should be molded such that total volume in the valve 10 when the valve 10 is in the open mode is greater than the total volume when in the closed mode. Alternatively, to create a substantially neutral fluid displacement, the resilient member 310 should be formed/molded such that the total volume when in the closed mode and the open mode are substantially equal.

It is important to note that, although FIGS. 6 and 7 show an embodiment of the control member 340 having seven leg members 370 spaced equally around the control member 340, other embodiments of the control member 340 may have a different number of legs. For example, some embodiments may have three leg members 370, while others may have four or more. Additionally, the leg members 370 need not be spaced equally around the control member 340. For example, the leg members 370 may be spaced and/or aligned in any manner that keeps the distal aperture 338 closed (and the body portion 330 sufficiently compressed) when the valve 10 is in the closed mode. It is also important to note that the number, spacing, and the size of the leg members 370 may be configured such that the resilient member 310 is unable to squeeze between the leg members 370, which may hinder performance of the valve 10.

Additionally, some embodiments of the present invention may not utilize a control member 340 with the leg members 370 described above. In such embodiments, the valve 10 may include a control member 340 with an interrupted wall (not shown). For example, the wall may have interruptions spaced about the diameter of the control member 340 to create alternating areas of wall material and interruptions. Like the embodiments having leg members 370 described above, the interrupted wall may also have thinned areas that allow the interrupted wall to deform/flex more easily as the valve 10 transitions between the closed and open modes.

Furthermore, other embodiments of the present invention may have a control member 340 with a solid wall (e.g., no interruptions or leg members 370). In such embodiments, like the embodiments having leg members 370 and interruptions, the solid wall may have one or more thinned portions that allow the solid wall to deform/flex more easily as the valve 10 transitions between the closed and open modes.

It is also important to note that, although FIG. 5 shows a resilient member 310 with a circular cross section, the resilient member 310 may have different shaped cross-sections. For example, in some embodiments, the resilient member 310 may have an elliptical cross-section. In such embodiments, the leg members 370 may be spaced such that they apply a compressive force to the major axis to close the distal aperture 338 when the valve 10 is in the closed mode and the resilient member 310 is in the compressed/deformed state.

Accordingly, acting against the conventional wisdom of those in the art, the inventors discovered that volumes within the fluid path may be controlled more effectively by forming the resilient member 310 with a radially expanded, longitudinally smaller body portion 330. In this manner, the open mode volume of the body portion 330 is known and thus, more controllable.

This is contrary to open mode volumes of various prior art valves, which deform in a manner that can be difficult to predict. Moreover, the closed volume of the body portion 330 also is more controllable since it is known at assembly. Accordingly, the open and closed mode volumes are more readily controllable, thus enabling the relative volumes to be tuned to the needs of the application (during design).

Although the above discussion discloses various exemplary embodiments of the invention, it should be apparent that those skilled in the art can make various modifications that will achieve some of the advantages of the invention without departing from the true scope of the invention.

What is claimed is:

1. A medical valve having an open mode that permits fluid flow, and a closed mode that prevents fluid flow, the medical valve comprising:
   a housing having an inlet and an outlet;
   a control member located within the housing and having a control member body portion with an outer radial width, a first length when the valve is in the closed mode and a second length when the valve is in the open mode, the first length being greater than the second length, the outer radial width radially expanding due to insertion of a medical implement into the inlet to transition the valve from the closed mode to the open mode; and
   a resilient member within the housing and having a resilient member body portion, the control member at least in part containing the resilient member body portion, the resilient member body portion being formed with a free state when undeformed by the control member and having a deformed state when the valve is in the closed mode, the resilient member body portion being formed to radially expand to return toward the free state to an open state as the valve transitions from the closed mode to the open mode, expansion of the outer radial width of the control member allowing the resilient member body portion to return toward the free state to the open state, the resilient member body portion defining at least part of a fluid path through the valve.

2. A medical valve according to claim 1, wherein the resilient member body portion and housing are configured to permit the resilient member body portion to attain the free state when in the open mode.

3. A medical valve according to claim 1, wherein the resilient member body portion is molded in the free state.

4. A medical valve according to claim 1, wherein the resilient member body portion is normally biased radially outwardly in the closed mode.

5. A medical valve according to claim 1, wherein the resilient member further includes a proximal seal portion having a normally closed aperture therethrough, the resilient member body portion being distal to the proximal seal portion.

6. A medical valve according to claim 1, wherein the resilient member body portion has a distal aperture therethrough, the distal aperture biased toward the open state, the distal aperture being closed when in the deformed state to prevent fluid flow through the valve.

7. A medical valve according to claim 6, wherein the distal aperture is molded open.

8. A medical valve according to claim 1, wherein the control member includes a plurality of leg members, the leg members radially deforming to expand the control member as the valve transitions toward the open mode to allow the resilient member body portion to return towards the free state to the open state.

9. A medical valve according to claim 8, wherein the leg members bias the valve toward the closed mode.

10. A medical valve according to claim 1, wherein the control member includes a biasing member, the biasing member biasing the valve toward the closed mode.

11. A medical valve according to claim 10, wherein the biasing member is a leaf spring.

12. A medical valve according to claim 1, wherein the resilient member body portion has a radial width when in the free state, the control member deforming the resilient member body portion when in the open state such that the radial width when the resilient member body portion is in the open state is greater than the radial width when the resilient member body portion is in the free state.

13. A medical valve according to claim 1, wherein the valve has a substantially neutral fluid displacement at the outlet as the valve transitions from the open mode to the closed mode.

14. A medical valve having an open mode that permits fluid flow, and a closed mode that prevents fluid flow, the medical valve comprising:
    a housing having an inlet and an outlet;
    a control member located within the housing and having a control member body portion with an outer radial width, a first length when the valve is in the closed mode and a second length when the valve is in the open mode, the first length being greater than the second length, the outer radial width radially expanding due to insertion of a medical implement into the inlet to transition the valve from the closed mode to the open mode; and
    a resilient member within the housing and having a proximal aperture and a distal aperture, the resilient member begin formed with a free state when undeformed by the control member and in which the distal aperture is biased toward an open state to allow fluid flow through the valve when in the open mode, the resilient member being deformed by the control member when the valve is in the closed mode to close the distal aperture and prevent fluid flow through the valve, the resilient member returning toward the free state such that the distal aperture returns to its open state as the valve transitions from the closed to open mode, expansion of the outer radial width of the control member allowing the resilient to return toward the free state and the distal aperture to return to the open state.

15. A medical valve according to claim 14, wherein the distal aperture is formed to be in the open state when no radial force is applied to the resilient member.

16. A medical valve according to claim 14, wherein the distal aperture is molded in the open state.

17. A medical valve according to claim 14, wherein the control member includes a plurality of leg members, the leg members radially deforming to expand the control member as the valve transitions toward the open mode.

18. A medical valve according to claim 17, wherein the leg members bias the valve toward the closed mode.

19. A medical valve according to claim 14, wherein the control member includes a biasing member, the biasing member biasing the valve toward to closed mode.

20. A medical valve according to claim 19, wherein the biasing member is a leaf spring.

21. A medical valve according to claim 14, wherein the resilient member includes a resilient member body portion with the free state when undeformed by the control member and a deformed state when the valve is in the closed mode, the resilient member body portion being formed to return toward the free state as the valve transitions from the closed mode to the open mode, the resilient member body portion defining at least part of a fluid path through the valve.

22. A medical valve according to claim 21, wherein the resilient member further includes a proximal seal portion, the resilient member body portion being distal to the proximal seal portion, the distal aperture being located within the resilient member body portion and the proximal aperture being located within the proximal seal portion.

23. A method comprising:
connecting a medical valve to a patient, the medical valve comprising a housing having an inlet and an outlet, a control member having a control member body portion with an outer radial width, a first length when the valve is in a closed mode and a second length when the valve is in an open mode, the first length being greater than the second length, the valve also having a resilient member within the housing, the resilient member being formed with a free state when undeformed by the control member and having a proximal aperture and a distal aperture, the control member deforming the resilient member to close the distal aperture when the valve is in a closed mode;
inserting a medical implement through the inlet;
moving the medical implement distally within the housing to transition the valve from the closed mode to an open mode, distal movement of the medical implement causing the outer radial width to expand generally radially to allow the resilient member to return toward the free state and the distal aperture to return to the open state; and
transferring fluid between the medical implement and the patient through the valve.

24. A method according to claim 23, wherein the distal aperture is formed to be in the open state when no radial force is applied to the resilient member.

25. A method according to claim 23, wherein the control member includes a plurality of leg members, the leg members radially deforming to expand the control member as the valve transitions toward the open mode.

26. A method according to claim 23, wherein the control member includes a biasing member, the biasing member biasing the valve toward to closed mode.

27. A method according to claim 23 wherein the distal aperture is in the open state when the valve is in the open mode.

28. A method according to claim 23 wherein the resilient member attains the free state when the valve is in the open mode.

29. A medical valve according to claim 14 wherein the distal aperture is in the open state when the valve is in the open mode.

30. A method according to claim 14 wherein the resilient member attains the free state when the valve is in the open mode.

31. A medical valve according to claim 1, wherein the resilient member body portion has a radial width when in the free state and the open state, the radial width when the resilient member body portion is in the open state being equal to the radial width when the resilient member body portion is in the free state.

32. A medical valve according to claim 1, wherein the resilient member body portion is in the open state when the valve is in the open mode.

33. A medical valve according to claim 1, wherein the resilient member body portion is in the free state when undeformed by mechanical forces.

34. A medical valve according to claim 1, wherein the control member substantially surrounds the resilient member body portion.

35. A medical valve according to claim 14, wherein the control member substantially surrounds at least a portion of the resilient member.

36. A medical valve according to claim 23, wherein the control member substantially surrounds at least a portion of the resilient member.

37. A medical valve according to claim 1, wherein the control member is configured to apply a radially inward force to decrease a radial dimension of the resilient member body portion as the valve transitions from the open mode to the closed mode.

38. A medical valve according to claim 6, wherein the resilient member further includes a proximal seal portion having a proximal normally closed aperture therethrough, the resilient member body portion being distal to the proximal seal portion and the proximal normally closed aperture being spaced from distal aperture.

39. A medical valve according to claim 1, wherein the control member body portion has a proximal end and a distal end, the first length being a distance between the proximal end and the distal end when the valve is in the closed mode, the second length begin a distance between the proximal end and the distal end when the valve is in the open mode.

40. A medical valve according to claim 14, wherein the control member body portion has a proximal end and a distal end, the first length being a distance between the proximal end and the distal end when the valve is in the closed mode, the second length begin a distance between the proximal end and the distal end when the valve is in the open mode.

41. A method according to claim 23, wherein the control member body portion has a proximal end and a distal end, the first length being a distance between the proximal end and the distal end when the valve is in the closed mode, the second length begin a distance between the proximal end and the distal end when the valve is in the open mode.

* * * * *